United States Patent [19]

Altman et al.

[11] Patent Number: 4,636,463
[45] Date of Patent: Jan. 13, 1987

[54] ANTIBODIES TO HUMAN INTERLEUKIN-2 INDUCED BY SYNTHETIC POLYPEPTIDES

[75] Inventors: Amnon Altman, San Diego; Argyrios N. Theofilopoulos, La Jolla; Richard A. Lerner, La Jolla; Frank J. Dixon, La Jolla, all of Calif.

[73] Assignee: Scripps Clinic and Research Foundation, La Jolla, Calif.

[21] Appl. No.: 597,179

[22] Filed: Apr. 5, 1984

[51] Int. Cl.$^4$ .................. C07C 103/52; G01N 33/531; G01N 33/535
[52] U.S. Cl. .................................... 435/7; 210/502; 424/88; 435/810; 436/547; 436/808; 436/823; 530/351; 530/300
[58] Field of Search ............... 436/547, 808, 823; 260/112 R, 112.5 R, 112 B; 435/7, 810; 210/502; 424/88

[56] References Cited

U.S. PATENT DOCUMENTS

| | | | |
|---|---|---|---|
| 4,218,436 | 8/1980 | Fitzpatrick | 436/823 X |
| 4,438,030 | 3/1984 | Garfield | 260/112.5 R |
| 4,473,493 | 9/1984 | Gillis | 260/112 R |
| 4,478,744 | 10/1984 | Mezei | 260/112.5 R |
| 4,493,795 | 1/1985 | Nestor | 260/112.5 R |
| 4,518,584 | 5/1985 | Mark | 260/112.5 R X |

OTHER PUBLICATIONS

R. J. Robb et al., Proc. Natl. Acad. Sci. USA, 80(19), 5990–5994 (Oct. 1983).
R. Devos et al., Nucleic Acids Research, 11(13), 4307–4323 (1983).
T. Taniguchi et al., Nature, 302(5906), 305–310 (1983).
Chemical Abstracts, 100: 97628e (1984).
Lerner, Nature, 229, 592–596 (1982).
Sutcliffe et al., Nature, 287, 801–805 (1980).
Green et al., Cell, 28, 477–487 (1982).
Lerner et al., Proc. Natl. Acad. Sci. USA, 78, 3403–3407 (1981).
Smith and Pease, CRC Critical Reviews in Biochemistry, vol. 8, 315–399 (1980).
Sternberg and Thornton, Nature, 271, 15–19 (1978).
Schulz et al., Nature, 250, 140–142, (1974).
Argos et al., Biochimica et Biophysica Acta, 439, 261–273 (1976).
Matthews, Biochimica et Biophysica Acta, 405, 442–451 (1975).
Atassi et al., Proc. Natl. Acad. Sci. USA, 80, 840–844 (1983).

Primary Examiner—Sidney Marantz
Attorney, Agent, or Firm—Dressler, Goldsmith, Shore, Sutker & Milnamow, Ltd.

[57] ABSTRACT

Chemically synthesized polypeptides containing about 6 to about 40 amino acid residues having amino acid residue sequences that substantially correspond to the amino acid residue sequences of antigenic determinants of interleukin-2, when administered alone or as polymers or as conjugates bound to carriers, induce the production of antibodies of predetermined specificities. The polypeptides and the antibodies produced thereto can be used in diagnostic systems to measure the presence and amount of interleukin-2 and interleukin-2 cell surface receptors or binding sites in an assayed sample.

32 Claims, 9 Drawing Figures

```
1                    20                   40
·                    ·                    ·
MYRMQLLSCIALSLALVTNSAPTSSSTKKTQLQLEHLLLDLQMILNGINNY
                  ─────────────C
                       P81
                     (18-32-C)

60                   80                   100
          ·                    ·                    ·
KNPKLTRMLTFKFYMPKKATELKHLQCLEEELKPLEEVLNLAQSKNFHLRP
──────────C              ─────────      ─────────
   P83            ──────────    P84          P11
 (51-64-C)           P10     (79-92)      (94-108-C)
                   (65-78)
               120                  140
                ·                    ·
RDLISNINVIVLELKGSETTFMCEYADETATIVEFLNRWITFCQSIISTLT
───C ──────────          ─────────       ─────────
       P12        C──────────              P82
    (111-125)         P13                (139-153)
                   (C-126-138)
```

FIG. 1

```
           (18)    (20)                              (30)     (32)
    P81   ThrAsnSerAlaProThrSerSerSerThrLysLysThrGlnLeuCys

(51)                      (60)            (64)
    P83   TyrLysAsnProLysLeuThrArgMetLeuThrPheLysPheCys

(65)          (70)                    (78)
    P10   TyrMetProLysLysAlaThrGluLeuLysHisLeuGlnCys

(79)                              (90)   (92)
    P84   LeuGluGluGluLeuLysProLeuGluGluValLeuAsnLeu

(94)            (100)                  (108)
    P11   GlnSerLysAsnPheHisLeuArgProArgAspLeuIleSerAsnCys (111)                    (120)         (125)
    P12   ValIleValLeuGluLeuLysGlySerGluThrThrPheMetCys (126)    (130)                        (138)
    P13    CysGluTyrAlaAspGluThrAlaThrIleValGluPheLeu (139)                         (150)      (153)
    P82   AsnArgTrpIleThrPheCysGlnSerIleIleSerThrLeuThr
```

FIG. 2

ANTIBODIES TO HUMAN INTERLEUKIN-2 INDUCED BY SYNTHETIC POLYPEPTIDES

DESCRIPTION

1. Technical Field

The present invention relates to (a) chemically synthesized polypeptides, polymers of the polypeptides and conjugates of the polypeptides bound to a carrier, each polypeptide including an amino acid residue sequence that substantially corresponds to the amino acid residue sequence of an epitope or a determinant portion of a lymphokine, specifically, interleukin-2; (b) methods for preparation and use of the polypeptides and the antibodies produced therefrom; and (c) diagnostic systems for measuring the presence and amount of interleukin-2 in an assayed sample.

2. Background

The immune response involves complex interactions among various effector and regulatory cells of the reticuloendothelial system. Thymus-derived lymphocytes, or T cells, play a significant role in these interactions. T cells mediate several effector functions, such as lysis of target cells by macrophages, and also regulate humoral and cell-mediated immune responses. Once it was established that T helper cells collaborate with B cells in antibody responses, immunologists began searching for soluble factors that mediate such interactions.

Dutton et al., Prog. Immunol., 1, 355 (1971), reported a soluble product or factor that acted as a signal between the cells producing the factor and other cells having the relevant acceptor sites. That study demonstrated the ability of a factor to augment antibody response and was followed by numerous similar studies. It is now well documented that soluble factors produced predominantly by activated T cells have profound regulatory effects on the immune system. Altman et al., Adv. Immunol., 33, 74 (1982).

The soluble factors of lymphocytes that are responsible for the multiple effects of a cellular immune reaction are called lymphokines. Until recently, lymphokines were defined by their biological activity in a particular assay; i.e., functionally, rather than by particular biochemical and biological properties. That approach resulted in an imprecise and often redundant system of nomenclature.

To remove constraints associated with assay derived definitions, a new system of describing lymphokines was developed. That system is based on a number of independent and collaborative studies that clearly demonstrate that several lymphokine activities are in fact different biological facets of a single biochemical entity. See, for example, Aarden et al., J. Immunol., 123, 2928 (1979). The term "Interleukin" (meaning "between lymphocytes") was selected to designate those lymphokines that have the ability to act as signals between different populations of lymphocytes.

The lymphokine specifically of interest herein is Interleukin-2 (IL-2), formerly known as T Cell Growth Factor (TCGF). A mechanism for the production and action of IL-2 has been proposed by Smith, Immunol. Rev., 51, 337 (1980). According to that model, macrophages are activated by an antigen to produce Interleukin-1 (IL-1). The antigen can be a particular substance to which the cell has been sensitized or non-specific mitogen such as phytohemagglutinin (PHA), Concanavalin A (Con A) or pokeweed mitogen (PWM). The antigen, together with IL-1, provides a differentiation signal to a set of T cells. This differentiation results in IL-2 production and secretion.

At the same time, the antigen, with or without the macrophage-dependent signal, stimulates another set of T cells to display surface receptors for IL-2. Interactions between IL-2 and its cellular receptors result in proliferation of T cells belonging to the different functional subsets. Thus, IL-2 provides the universal signal for T cell proliferation.

Given its essential role in immune responses, it is not surprising that defects in the level and activity of IL-2 have been discovered in a variety of disease states. Altman et al., J. Exp. Med., 154, 791 (1981), reported that autoimmune murine strains displaying systemic lupus erythematosus (SLE) have a profound defect in IL-2 production and responsiveness. These findings were later demonstrated in humans with SLE by Varela et al., J. Clin. Invest., 69, 1388 (1982) and Linker-Israeli et al., J. Immunol., 130, 2651 (1983).

IL-2 defects have also been found in aged mice and humans. Thoman et al., J. Immunol., 128, 2358 (1982) and Gillis et al., J. Clin. Invest. 67, (1981). Similar defects have been reported in children suffering from primary immunodeficiencies [Flomerberg et al., J. Immunol., 130, 2644 (1983)], in recipients of allogenic bone marrow transplants, [Warren et al., J. Immunol., 131, 1771 (1983)], and in parasite-infected mice [Reiner et al., J. Immunol., 131, 1487 (1983)]. Such defects are also strongly suspected in acquired immune deficiency syndrome (AIDS), malignant disease and in certain viral infections.

Some of the biological effects of IL-2 have possible therapeutic significance. One example is the ability of IL-2 to induce or augment the activity of several types of killer cells including cytotoxic T lymphocytes (CTL) [Wagner et al., Immunol. Rev., 51, 215 (1980)], natural killer (NK) cells [Henney et al., Nature, 291, 335 (1981)] and lymphokine-activated killer (LAK) cells [Grimm et al., J. Exp. Med., 155, 1823 (1982)]. Each of these killer cells can lyse tumor target cells in vitro and is implicated as an in vivo effector cell in the determination and surveillance of malignancies.

Furthermore, it has recently been shown that purified IL-2 will augment the efficiency of sensitized T cells and chemotherapeutic agents by causing the regression of an established T cell leukemia in mice. Cheever et al., J. Exp. Med., 155, 968 (1982).

Reagents that can detect the presence of a lymphokine serologically, as opposed to monitoring its biological effect, would be valuable in diagnosing disease and in developing immunotherapeutic agents for T cell-associated immunodeficiencies. In particular, antibodies reactive with IL-2 can make possible definitive studies of IL-2 biological activity, immunopurification, the development of IL-2 immunoassays, the identification of the active site of the molecule, and an array of in vivo studies to determine the physiological role of IL-2 in the immune response.

Recent reports suggest that it is possible to develop monoclonal antibodies reactive with IL-2. To date, the major problem in the development of these antibodies is the difficulty of accumulating enough IL-2 protein in a purified and concentrated form so that immunization and serologic assay become feasible. Although it is not essential to immunize with homogeneous IL-2 to obtain anti-IL-2 activity, it is important to immunize with at least microgram quantities of the IL-2 protein. The development of an immunoassay that recognizes anti-IL-2 activity, however, does require the use of relatively pure IL-2.

The difficulty in obtaining purified quantities of IL-2 reflects two shortcomings of conventional IL-2 preparation techniques. First, multiple lymphokines may be secreted by a single cloned T cell source. This makes the isolation of a particular lymphokine rather difficult. Second, purification procedures involve several steps and require relatively large volumes of IL-2-containing culture media.

A further example of the potential therapeutic value of IL-2 is its ability to induce, together with an antigen, functional cell-mediated immunity in athymic nude mice. Wagner et al., Nature, 248, 278 (1980). An athymic nude mouse is a hairless mouse that congenitally lacks a thymus and has a marked deficiency of thymus-derived lymphocytes (T cells). This finding further suggests that IL-2 may have an immunotherapeutic potential in certain states of T cell-associated immunodeficiencies.

BRIEF SUMMARY OF THE INVENTION

The present invention relates to the preparation of antibodies to human interleukin-2 (IL-2), using as immunogens relatively short synthetic polypeptides having amino acid residue sequences that substantially correspond to portions of the amino acid residue sequence of IL-2. In particular, eight polypeptides (see FIGS. 1 and 2) consisting of 13 to 15 amino acids were chemically synthesized. These synthetic polypeptides are referred to herein as "IL-2 polypeptides".

The IL-2 polypeptides were conjugated to a protein carrier and were used to immunize both rabbits and mice. The resulting immune sera were screened in a solid phase enzyme-linked immunosorbent assay (ELISA) for reactivity to a partially-purified tonsil-derived human IL-2. Antibodies, specifically oligoclonal antibodies, induced by four of the eight polypeptides were found to react against (bind to) human IL-2.

The synthetic polypeptides of the present invention contain from about 6 to about 40 amino acid residues, preferably from about 10 to about 20 amino acid residues, and include an amino acid sequence that substantially corresponds to an amino acid residue sequence of an antigenic determinant of interleukin-2. Each synthetic polypeptide has the capacity alone, as a polymer or as a conjugate bound to a carrier when injected into a host in an effective amount and in a physiologically tolerable diluent of inducing the production of antibodies to an antigenic determinant of IL-2.

In particular, antibodies induced by the following four polypeptides (taken from left to right and in the direction of amino-terminus to carboxy-terminus) were found to bind to human IL-2:

ThrAsnSerAlaProThrSerSerSerThrLysLysThrGlnLeu;
LeuGluGluGluLeuLysProLeuGluGluValLeuAsnLeu;
ValIleValLeuGluLeuLysGlySerGluThrThrPheMetCys; and
AsnArgTrpIleThrPheCysGlnSerIleIleSerThrLeuThr.

An oligoclonal antibody, as defined herein, is an immunoglobulin product of an immune response that is induced by and binds to an epitope on a polypeptide of moderate length including about 6 to about 40 amino acid residues. Oligoclonal antibodies are usually a mixture of receptors produced by more than one cell. Oligoclonal receptors so produced are usually more epitopically specific in their binding than are the polyclonal receptors raised to whole protein molecules that can have epitopic regions throughout the length of the protein chain or chains. Animals immunized with the polypeptides useful herein produce sera containing oligoclonal receptors (antibodies).

The reactivity of these antibodies with IL-2 was confirmed by the following studies: (a) identical profiles of IL-2 biological activity and immunoreactivity were observed following three consecutive and independent chromatographic studies of a crude IL-2 supernatant; (b) anti-polypeptide and anti-IL-2 activities were eluted in the same fractions from a peptide immunoaffinity column; (c) affinity-purified anti-IL-2 polypeptide antibodies bound to electrophoretically-pure human IL-2 derived from the Jurkat Leukemic T cell line; and (d) on sodium dodecyl sulfate (SDS) gels, an affinity-purified rabbit antibody induced by one of the IL-2 polypeptides (P84) immunoprecipitated a protein of 15,000–18,000 daltons, as determined by Western blot analysis.

Moreover, IL-2 biological activity was eluted from an almost identical position in the gel. Affinity-purified anti-P84 antibody specifically stained the cytoplasm of phytohemagglutinin (PHA)-stimulated human peripheral blood lymphocytes (PBL). And the anti-IL-2 polypeptide antibodies bound to pure human recombinant IL-2 (also known as recombin-ant IL-2) in an ELISA procedure.

The present invention also relates to monoclonal antibodies which are receptors produced by clones of a single cell fused from an antibody-producing cell and a myeloma or other self-perpetuating cell line that secretes only one receptor molecule. Such receptors were first described by Kohler and Milstein, Nature, 256, 495 (1975), which description is incorporated reference.

As demonstrated herein, oligoclonal and monclonal antibodies to synthetic IL-2 polypeptides are useful probes for studying interleukin-2, and for developing quantitative assays for measuring levels of IL-2 in biological fluids and the association of such levels with disease.

In particular, one embodiment of this invention relates to a diagnostic system for assaying for the presence of an antigenic determinant of interleukin-2. This system includes a first package containing the oligoclonal or monoclonal antibodies of this invention. When a predetermined amount of those antibodies is admixed with a predetermined amount of an aqueous composition containing IL-2, a complex is formed by an immunological reaction. The presence of the complex can be determined by a label that is preferably contained in a second package of the system.

In yet another embodiment of this invention, oligoclonal or monoclonal antibodies form the active, binding portions of an affinity-sorbant useful for binding and purifying interleukin-2. Here, the antibodies are linked to a solid support that is chemically inert to IL-2 such as agarose or cross-linked agarose. The affinity sorbant so prepared can then be admixed with an IL-2-containing aqueous composition to form a reversible antibody-antigen complex that can thereafter be dissociated to provide IL-2 in a purified form.

Still further advantages, benefits and uses of the present invention will become apparent to those skilled in the art from the detailed description, examples and claims which follow.

BRIEF DESCRIPTION OF THE DRAWINGS

In the drawings, which constitute a portion of this disclosure:

FIG. 1 illustrates the 153 amino acid sequence of interleukin-2 as determined by Taniguchi et al., Nature, 302, 309 (1983). Regions of the protein selected for synthesis according to the present invention are indicated by underlining. The letter C at either end of an underline indicates the addition of a cysteine not found in the primary sequence. The following single letter and conventional three letter codes (see FIG. 2) correspond to the indicated amino acids: A, Ala (L-Alanine); C, Cys (L-Cysteine); D, Asp (L-Aspartic acid); E, Glu (L-Glutamic acid); F, Phe (L-Phenylalanine); G, Gly (Glycine); H, His (L-Histidine); I, Ile (L-Isoleucine); K, Lys (L-Lysine); L, Leu (L-Leucine); M, Met (L-Methionine); N, Asn (L-Asparagine); P, Pro (L-Proline); Q, Gln (L-Glutamine); R, Arg (L-Arginine); S, Ser (L-Serine); T, Thr (L-Threonine); V, Val (L-Valine); W, Trp (L-Tryptophan); and Y, Tyr (L-Tyrosine).

FIG. 2 illustrates the amino acid sequences of polypeptides designated P81 (residues 18-32 with a carboxy-terminus cysteine); P83 (residues 51-64 with a carboxy-terminus cysteine); P10 (residues 65-78); P84 (residues 79-92); P11 (residues 94-108 with a carboxy-terminus cysteine); P12 (residues 111-125); P13 (residues 126-138 with an amino-terminus cysteine); and P82 (residues 139-153) using the conventional three letter code as indicated above for each amino acid. Each of the residue position numbers is based upon the positions taken from left to right and in the direction from amino-terminus to carboxy-terminus of the IL-2 molecule shown in 1.

DETAILED DESCRIPTION OF THE INVENTION

I. Introduction

Figure 3:
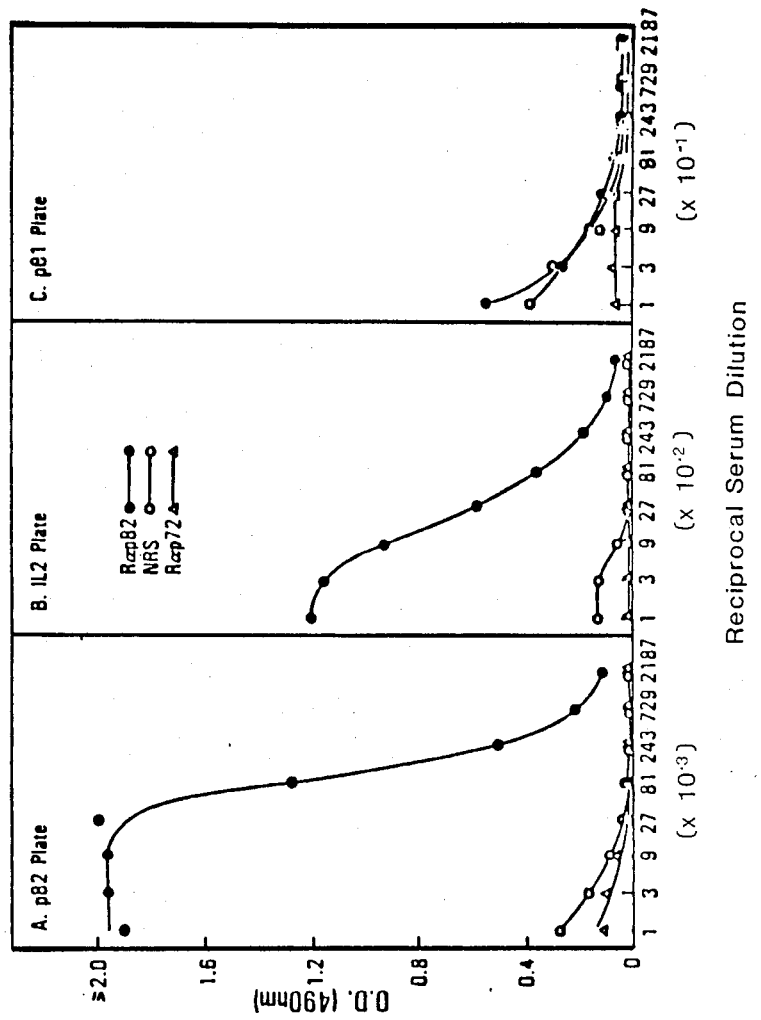
FIG. 3 shows a series of three graphs (panels A, B and C) that illustrate the specificity of rabbit anti-P82 serum in enzyme-linked immunosorbent assays [ELISAs]. Rabbit anti-P82 serum (RαP82); the preimmune serum (normal rabbit serum) from the same rabbit (NRS); and a hyperimmune rabbit anti-hepatitis B polypeptide (RαP72) serum were titrated on plates coated with P82 (panel A), partially purified tonsil IL-2 preparation (panel B), or P81 (panel C). Values are given after subtraction of background reactions on BSA-coated plates.

Interleukin-2 (IL-2), also known as T cell growth factor (TCGF), is a T cell-derived glycoprotein. IL-2 is believed to provide a universal signal for the proliferation of mature T cells [Smith, Immunol. Rev., 51, 337 (1980)] through its binding to specific cell surface receptors [Robb et al., J. Exp. Med., 154, 1455 (1981)]. Originally, IL-2 was shown to support the long-term growth of lectin-activated T cells [Morgan et al., Science, 128, 821 (1976) and Ruscetti et al., J. Immunol., 119, 131, (1977)]. The discovery of IL-2 lead to the establishment of functional, antigen-specific T-cell lines [Gillis et al., Nature, 268, 154 (1977)].

Recent progress in IL-2 research has resulted in the development of B cell hybridomas producing monoclonal antibodies to human IL-2 [Smith et al., J. Immunol., 131, 1808 (1983); and Robb et al., Proc. Natl. Acad. Sci. (USA), 80, 5990 (1983)]; and the molecular cloning of a human complimentary DNA (cDNA) that can be expressed and translated into a biologically-active IL-2 [Taniguchi et al., Nature, 302, 305 (1983)].

Despite the rapid progress in this area, the structure-function relationships of IL-2 remain unknown; for example, the particular amino acid residues involved in the active site(s) are not yet known. Furthermore, although a sensitive and reliable IL-2 bioassay as described in Gillis et al., J. Immunol, 120, 2027 (1978) is available, that assay is susceptible to a variety of inhibitory materials that may preclude its routine use for the quantitation of IL-2 in biological fluids.

Recent studies have shown that synthetic polypeptides can be used to induce antibodies specific for predetermined primary amino acid residue sequences in intact proteins as described in Lerner R.A., Nature, 299, 592 (1982) and Sutcliffe et al., Science, 219, 260 (1983). Such antibodies can be raised even against polypeptides that are not immunogenic in the context of the native protein molecule.

Anti-polypeptide antibodies are, therefore, powerful tools for analyzing the fine structure of complex proteins. The present invention employs such methodology of raising antibodies to synthetic polypeptides. Antibodies are raised against several synthetic polypeptides derived from the published amino acid residue sequence of a human IL-2 molecule as described in Taniguchi et al, Nature, 302, 305, (1983). Also described is the determination of the properties of such antibodies and evidence that the anti-polypeptide antibodies recognize and bind to (react with) human IL-2.

A synthetic polypeptide in accordance with this invention has an amino acid residue sequence of contiguous amino acids that substantially corresponds immunologically to the amino acid sequence of an antigenic determinant of interleukin-2. The polypeptide contains from about 6 to about 40 amino acid residues and preferably from about 10 to about 20 amino acid residues. The polypeptide, when administered alone or as polymer or as a conjugate bound to a carrier such as keyhole limpet hemocyanin (KLH) or the like and introduced in an effective amount in a physiologically tolerable diluent vehicle into a host animal, induces the production of anti-polypeptide antibodies in the host.

Throughout the application, the terms "peptide" and "polypeptide" are used interchangeably. The term "synthetic polypeptide" means a chemically built-up, as compared to a biologically built and degraded, chain of amino acid residues that is free of naturally occurring proteins and fragments thereof. Such synthetic polypeptides can elicit production of anti-polypeptide antibodies in a host.

The phrase "immunologically corresponds substantially" in its various grammatical forms is used herein and in the claims in relation to polypeptide sequences to mean that the polypeptide sequence described induces production of antibodies that bind to the polypeptide and to the antigenic determinant.

The term "substantially corresponds" in its various grammatical forms is used herein and in the claims in relation to polypeptide sequences to mean the polypeptide sequence described plus or minus up to three amino acid residues at either or both of the amino- and carboxy-termini and containing only conservative substitutions in particular amino acid residues along the polypeptide sequence.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

According to a method of the present invention, a suitable host is treated with an effective amount of a synthetic polypeptide in a physiologically tolerable diluent, the polypeptide having an amino acid residue sequence that immunologically corresponds substantially to an amino acid sequence of an antigenic determinant of interleukin-2. Anti-polypeptide antibodies are thus produced that can recognize and bind to an antigenic determinant of interleukin-2.

In this manner, the resulting "anti-polypeptide antibody" has a predetermined specificity and has substantially the same configuration as an antibody that binds to the antigenic determinant of IL-2. Antibodies of this type provide an improved means for defining the structure of antigenic determinants, as well as providing means for diagnostics and therapy.

The word "receptor" is used herein to mean an antibody in substantially pure form such as in the serum of an immunized animal or the idiotype-containing polyamide portion of an antibody (an antibody combining site) in substantially pure form. Receptors useful herein bind at least with an antigenic determinant of interleukin-2 when admixed therewith in aqueous solution or solid phase, at least at physiological pH values and ionic strengths. Preferably, the receptors also bind to such an antigenic determinant within a pH value range of about 5 to about 9, and at ionic strengths such as that of distilled water to that of about one molar sodium chloride.

Idiotype-containing polyamide portions of antibodies are those portions of antibodies that bind to the epitope of the antigenic molecule. Such portions include the Fab, Fab' and F(ab')$_2$ fragments prepared from antibodies by well-known enzymatic cleavage techniques. See for example, U.S. Pat. No. 4,342,566 to Theofilopoulos and Dixon. Inasmuch as the antibodies from which idiotype-containing polyamides are obtained are described as raised against or induced by immunogens, idiotype-containing polyamide receptors will also be discussed as being "raised" or "induced" with the understanding that a cleavage step is required to obtain an idiotype-containing polyamide from an antibody.

The oligoclonal receptors of the present invention must be distinguished from previously prepared polyclonal receptors that were raised to a heterologous protein modified by a hapten. Those receptors typically were of low avidity as to the site of hapten modification and most of the antibodies were raised against the nonself, large protein molecule carrier.

The receptors can also be monoclonal. Techniques for preparing monclonal antibodies are well known. Monoclonal receptors useful in this invention can be prepared using a polypeptide as an immunogen as described in Niman et al., *Proc. Natl. Acad. Sci. USA*, 80, 4949 (1983). Monoclonal antibodies are typically obtained from hybridoma tissue cultures or from ascites fluid obtained from animals into which the hybridoma tissue was introduced.

The method of the present invention produces antibodies against synthetic polypeptides that mimic an antigenic determinant of a naturally occurring protein and result in a large fraction of the elicited sera being reactive against the natural protein.

According to another aspect of this invention, the method of producing antibodies against synthetic polypeptides can be used to raise antibodies against antigenic determinants that are not naturally immunogenic in the host. That is, certain portions of a macromolecule have the ability to be bound by an antibody (i.e., are antigenic) but do not elicit the production of antibodies (i.e., are not immunogenic).

Anti-polypeptide antibodies produced according to this invention therefore have several distinct advantages over antibodies produced by conventional immunization with an intact protein molecule.

The word "antigen" has been used historically to designate an entity that is bound by an antibody and to designate the entity that induces the production of the antibody. More current usage limits the meaning of antigen to that entity bound by an antibody, while the word "immunogen" is used for the entity that induces antibody production. In some instances, the antigen and immunogen are the same entity as where a synthetic polypeptide is utilized to induce production of antibodies that bind to the polypeptide. However, the same polypeptide can also be utilized to induce antibodies that also bind to a whole protein such as immunoglobulin, in which case the polypeptide is both immunogen and antigen, while the immunoglobulin is an antigen. Where an entity discussed herein is both immunogenic and antigenic, it will generally be termed an antigen.

In still a further aspect of this invention, diagnostic systems and methods are disclosed. These systems and methods utilize a polypeptide of this invention in the diagnostic system or method, or utilize that polypeptide to induce the production of a receptor of this invention that is utilized directly in the diagnostic system or method.

Yet another aspect of this invention contemplates affinity sorbents. Here, a polypeptide of this invention is utilized to induce the production of a receptor of this invention such as an antibody. That receptor is coupled to a support such as cross-linked dextran to form the affinity sorbant that can be used to obtain and purify naturally occurring IL-2 from body samples.

II. Production of Monoclonal Receptors

To successfully prepare monoclonal receptors that recognize both the immunogenic polypeptide and the IL-2 protein ligand to whose amino acid residue sequence that polypeptide corresponds in part, one should follow the steps outlined hereinbelow.

An immunogenic polypeptide of conjugate of that polypeptide bound to a carrier is provided. That polypeptide has an amino acid residue sequence of moderate length, such as about 6 to about 40 amino acid residues, and preferably about 10 to about 20 residues. The amino acid residue sequence of the immunogenic polypeptide corresponds to a portion of the amino acid residue sequence of a lymphokine such as IL-2. While the immunogenic polypeptide can be used by itself as a ligand, it is preferred to use the polypeptide immunogen as a conjugate bound to a carrier such as keyhole limpet hemocyanin (KLH), albumins such as bovine serum albumin (BSA), human serum albumin (HSA), red blood cells such as sheep erythrocytes, tetanus toxoid and edestin, as well as polyamino acids such as poly(D-lysine:D-glutamic acid), and the like.

The immunogenicity and antigenicity of the polypeptide may be tested by binding the polypeptide to a keyhole limpet hemocyanin carrier as a conjugate, and then using the conjugate so prepared to immunize a mouse. A useful polypeptide is sufficiently immunogenic and antigenic to produce a 50 percent binding titer of the immunized mouse's serum to the polypeptide that is at least about a 1:400 dilution after three immunizations in a one-month period, each of which immunizations contains at least about ten micrograms, and preferably at least about 50 micrograms, of the polypeptide in the conjugate, and utilizing complete Freund's adjuvant for the first immunization and alum as adjuvant thereafter.

This test procedure need not be carried out prior to the use of a given polypeptide as immunogen, but it is preferable to do so as a pre-screening technique to determine which polypeptides will be useful in preparing the desired monoclonal receptors. Whether used as a pre-screen or not, the polypeptides useful herein as immunogens provide the above titer using the above immunization regimen.

Upon provision of the immunogenic polypeptide, an animal such as a mouse, rabbit, goat, horse or the like is hyperimmunized with the immunogenic polypeptide or conjugate of that polypeptide bound to a carrier to provide a hyperimmune serum whose receptor molecules exhibit a 50 percent binding titer to the polypeptide of at least about a 1:400 dilution. Thus, the same animal, a mouse, in which one may desire to pre-test the immunogenicity of the peptide may be used for raising the Mabs.

It is noted that the immunization regimen required to provide a hyperimmune state is a function, inter alia, of the animal type, animal weight, the immunogenicity and amounts of the polypeptide and carrier, if used, the adjuvant, if used and the number of immunizations administered in a given time period, as is known. The above-described regimen for obtaining a 50 percent binding titer dilution of at least about 1:400 provides a hyperimmune state in the test mouse and may be used as a proportionalizable basis for inducing hyperimmune states in other animals. It is further noted that three immunizations are not necessarily required to provide the hyperimmunized state, but for a useful polypeptide, three such immunization in a one-month are sufficient to produce that state, or the polypeptide is not sufficiently immunogenic for the high yield production of hybridomas and their monoclonal antibodies of this invention.

The serum receptor molecules so produced in the hyperimmunized animal also bind to that portion of IL-2 to which the immunogenic polypeptide corresponds in amino acid residue sequence. These binding assays are described in the Materials and Methods Section hereinafter. It is noted that a pure sample of IL-2 need not be utilized in these assays but rather, a cell extract or tissue preparation such as a microscope slide containing IL-2 may be utilized.

The hyperimmunized animal is maintained; i.e., kept alive without administration of further immunizations for a period of at least about 30 days after administration of the immunization that produces a 50 percent binding titer of at least a 1:400 dilution. In other words, the animal is first immunized to provide a hyperimmunized state, and then the hyperimmunization is allowed to recede.

The decline in binding activity typically takes one to about five months for mice. This decline in binding titer is believed to correspond to a period in which primed blast cells become capable of mounting a vigorous response when the immunogen is again introduced.

A booster immunization, as by intravenous injection, using the immunogenic polypeptide or its conjugate is administered to the animal after the period of maintenance is completed, e.g. at least 30 days after the last immunization. Antibody-producing cells, such as spleen cells or lymph cells of the boosted animal are then fused with a myeloma cell line from the same or different animal type within a period of about three to about five days from the day of booster administration to prepare hybridoma cells. The boost is believed to stimulate the maturation of the blast cells to the point at which those cells secrete nearly optimal amounts of oligoclonal antibodies to the polypeptide.

The P3×63 or SP2/0, hypoxanthine-amino pterinthymidine(HAT)-sensitive, myeloma cell line is preferred for use in fusion with mouse spleen cells, although other cell lines may also be utilized. The hybridoma cells are thereafter cloned at limiting dilution free from the presence of, or need for, feeder layers or macrophages to reduce overgrowth by non-producing cells, and to provide a selection method for cells which grow readily under in vitro conditions.

The hybridoma cells so prepared are then assayed for the production (secretion) of monoclonal receptor molecules that bind to a determinant portion of IL-2 to which the immunogenic polypeptide corresponds in amino acid residue sequence. Thereafter, the hybridoma cells that produce monoclonal receptor molecules that bind to IL-2 are cultured further to prepare additional quantities of those hybridoma cells, and the monoclonal receptors secreted by those cells that bind to IL-2. Typically, such culturing is done at limiting dilution, e.g. at an average of about one cell per culture-growing well.

In preferred practice, the hybridoma cells that are prepared are also assayed for the production of monoclonal receptor molecules that bind to the polypeptide immunogen as well as to IL-2. Thereafter, hybridoma cells that produce monoclonal receptor molecules that bind to both the immunogenic polypeptide and to IL-2 are those cells that are preferably cultured.

Where samples of IL-2 are limited, it is convenient to first screen the hybridomas for secretion of monoclonal receptors that bind to the immunogenic polypeptide. Hybridoma clones that exhibit positive binding to that polypeptide are then frozen for storage. They are thereafter subcloned by limiting dilution for assurance that truely monoclonal antibodies are produced, rather than a plurality of monoclonal receptors being produced from a plurality of different hybridoma cells. Those limiting dilution subcloning cultures are again typically carried out free from feeder layers or macrophages, as such are not necessary.

The hybridoma cells that are ultimately produced may be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid are typically BALB/c mice bred in the mouse colony of the Scripps Clinic and Research Foundation, La Jolla, California, however, when animals other than mice are used for preparation of the hybridomas, mice or that animal type are used for the production of ascites fluid.

II. Discussion

The data presented herein demonstrate that antibodies reactive with native human IL-2 can be produced in rabbits and mice that are immunized with synthetic polypeptides derived from the known amino acid residue sequence of a human IL-2 molecule. This sequence was deduced from a recently cloned cDNA coding for human IL-2 [Taniguchi et al., supra] and was confirmed, at least partially, by direct protein sequencing [Smith et al., J. Immunol., supra and Robb et al., Proc. Natl. Acad. Sci. (USA), supra].

Several lines of evidence clearly demonstrate that the anti-polypeptide antibodies described herein recognize native human IL-2. First, anti-IL-2 polypeptide sera, but not the preimmune serum or a hyperimmune serum against an irrelevant polypeptide, bind to partially-purified, tonsil-derived IL-2 (as well as to the immunizing polypeptide). But anti-IL-2 polypeptide sera do not bind to an unrelated polypeptide or a mock IL-2 preparation. Moreover, the binding to IL-2 is specifically inhibited by the soluble immunizing polypeptide.

In addition, an excellent correlation between the profiles of biological activity and immunoreactivity is observed when crude IL-2-containing supernatants are fractionated by several independent steps based on different separation principles (i.e., AcA-44, Affi-gel blue or DEAE-Sephacel chromatographies).

Additional evidence presented herein that the anti-polypeptide antibodies of the present invention recognize native human IL-2 includes the following. (1) Anti-polypeptide and anti-IL-2 activity co-elute from a peptide immunoaffinity column. (2) Affinity-purified anti-polypeptide antibodies bind to electrofocused Jurkat-derived IL-2, which is considered to be essentially pure [Robb et al., J. Exp. Med., supra]. (3) IL-2 biological activity and an immunoreactive protein (identified by Western blot analysis) migrate in an almost identical position when a crude tonsil-derived, IL-2-containing supernatant is separated by SDS-PAGE. And (4) an affinity-purified antibody against one of the human IL-2 polypeptides produces a specific staining reaction on mitogen-activated human peripheral blood lymphocytes. Anti-IL-2 polypeptides bind to pure or recombinant IL-2 in an ELISA procedure. Taken together, these independent findings, which are explained more fully in the following Results section, demonstrate that the anti-polypeptide antibodies described herein recognize human IL-2 molecules.

Interestingly, the affinity-purified antibodies to polypeptides P12, P81, P82 or P84 did not neutralize the biological activity of human IL-2 and did not immunoprecipitate IL-2 from an IL-2-containing supernatant. This may be because an amino acid residue sequence necessary for biological activity is entirely or partially missing from the four polypeptides that elicited anti-IL-2 antibodies. The fact that a specific amino acid residue sequence may be necessary to elicit antibodies for viral protection or for inhibition of protein activity has previously been demonstrated with foot and mouth disease [Bittle et al., Nature, 298, 30 (1982)] and tyrosine-specific kinase activity of the pp60src transforming protein [Gentry et al., J. Biol. Chem., 258, 11219 (1983)], respectively.

On the other hand, the failure of certain of the antibodies to inhibit IL-2 activity, or to react with IL-2 in solution, may represent an affinity problem. For example, it has been shown that, even in the case of antibodies raised against native IL-2, a large excess of antibody is required to neutralize IL-2 activity [Smith et al., J. Immunol., 131, 1808 (1983)]. This is probably because the affinity of interaction between IL-2 and its cellular receptor [See Robb et al., supra] is greater by several orders of magnitude than the affinity of interaction between IL-2 and its respective antibody [Smith et al., supra]. The preparation of additional antibodies to other IL-2 polypeptides according to the method described herein, may clarify this issue.

The establishment of monoclonal hybridomas producing antibodies to human Jurkat-derived IL-2 has been recently reported. [Smith et al., supra and Robb et al., Proc. Natl. Acad. Sci. (USA), 80, 5990 (1983)]. As previously described, one of the critical requirements to ensure the production of such hybridomas is the use of sufficiently large quantities of purified IL-2 for immunization, thus requiring the preparation and processing of relatively large volumes of culture supernatants [Smith et al., supra].

The three monoclonal antibodies characterized by Smith et al. appeared to react with distinct epitopes on the IL-2 molecules, but these epitopes have not yet been identified. In the study by Robb et al., the monoclonal antibody appeared to react with a sugar moiety on the IL-2 molecule. This antibody reacted with Jurkat-derived IL-2, but not with tonsil-derived IL-2.

In contrast, the present invention involves the preparation of antibodies against predetermined primary amino acid residue sequences of the human IL-2 molecule. The decision to use synthetic polypeptides was based on the relatively recent understanding that, using synthetic polypeptides appropriately coupled to protein carriers, it is possible to elicit antibodies to practically any region of a protein molecule. That includes those regions that are not immunogenic in the context of the native molecule [Lerner, R.A., Nature, 299, 592 (1982)].

Such antibodies offer two important advantages. First, the use of an easily-prepared pure polypeptide eliminates the need for preparation of a sufficiently pure native antigen in the large quantities needed for immunization. Second, since the amino acid residue sequence of the synthetic polypeptide is known, the polypeptide can elicit the production of antibodies of predetermined specificity.

Moreover, since antibodies can be raised against synthetic primary amino acid residue sequences that are antigenically "silent" in the context of the native protein [Lerner, supra and Sutcliffe et al., Science, 219, 660 (1983)], the array of immunogenic epitopes and, therefore, the spectrum of antibodies to the IL-2 molecule, can be significantly expanded by the use of synthetic polypeptides. A particularly important illustration of the value of IL-2-reactive anti-polypeptide antibodies is their use to identify those polypeptide moieties in the IL-2 molecule that mediate biological function and/or binding to the cell surface receptors.

A significant example is a recently described antibody against a synthetic polypeptide deduced from the nucleotide sequence of a cloned src gene [Gentry et al., J. Biol. Chem., 258, 11219 (1983)]. Using this antibody, it was possible to identify a pentadecapeptide that is necessary for the biological activity (specifically, the tyrosine-specific kinase activity) of the transforming protein, pp60src.

Findings that anti-P84 antibodies can stain in a specific manner the cytoplasm of PHA-stimulated human PBL strongly suggests that these antibodies may serve as sensitive and reliable tools to enumerate IL-2-producing cells in relation to disease. This particular finding is analogous to that reported in a very recent study, using a monoclonal antibody made against native rat IL-2 [Steinman et al., Science, 220, 1188 (1983)].

In addition, changes in the primary amino acid residue sequence of IL-2 resulting from mutations or the like and leading to a loss or modification of biological activity, can theoretically be associated with certain diseases. If such IL-2 variants exist, anti-polypeptide antibodies may facilitate the identification of those variants.

The highly discriminatory power of anti-polypeptide antibodies has been clearly established. For example, such antibodies are able to discriminate between subtypes of the hepatitis B virus surface antigen [Gerin et al., Proc. Natl. Acad. Sci. (USA), 80, 2365 (1983)] and between idiotypic determinants in the hypervariable region of two dextran-binding myeloma proteins [McMillan et al., Cell, 35, 859 (1983)].

The ability of IL-2 to correct some immunodeficient states [Wagner et al., Nature, 284, 278 (1980)], to assist in tumor rejection in vivo [Cheever et al., J. Exp. Med., 155, 968 (1982)], and to enhance or stimulate the induction of CTL, NK and LAK cells in vitro has aroused great interest in this lymphokine and has suggested that IL-2 may provide an immunotherapeutic tool. Moreover, association of IL-2 abnormalities with various diseases has emphasized the need for sensitive and reliable quantitative immunoassays for human IL-2 in a clinical setting.

The relative ease in preparing anti-IL-2 antibodies by using synthetic IL-2-derived polypeptides indicates that such antibodies are useful in various studies of IL-2, including the establishment of more accurate lymphokine assays and the enumeration of lymphokine-producing cells in health and disease.

IV. Diagnostic Systems and Methods

It is often desirable to determine if a particular antigen is present in a biological sample as an aid, for example, in the diagnosis of a particular disease.

Exemplary diagnostic reagent systems include enzyme-linked immunosorbent assays (ELISA) wherein the indicator group is an enzyme such as horseradish peroxidase that is bound to an antibody, or radioimmunoassays in which the indicating group is a radioactive element such as $^{125}I$ present in either a synthetic polypeptide of the present invention or the antibody raised thereto.

According to the present invention, a diagnostic system for assaying for the presence of an antigenic determinant of interleukin-2 comprises in biochemically active form antibodies raised in an animal host to a synthetic polypeptide containing about 6 to about 40 amino acid residues and having an amino acid sequence that immunologically corresponds substantially to an amino acid sequence of an antigenic determinant of IL-2. In this diagnostic system, the above antibodies immunoreact with an admixed sample to be assayed to form an immunoreactant whose presence is signalled by an indicating means.

The indicating means can include enzyme-linked second antibodies that are raised to antibodies of the same class and from the same species of animal as the above first named antibodies. The indicating means signals the immunoreaction by binding to the first named antibodies present in the immunoreactant. In this system, the signal is indicated by the reaction of the linked enzyme with an added substrate. The indicating means can also include a radioactive element bonded to the antibodies.

Moreover, according to the present invention, a diagnostic system (preferably in kit form) for assaying for the presence of an antigenic determinant of a interleukin-2 in a body component includes in separate containers (a) a first reagent that contains in biologically active form a synthetic polypeptide of the present invention containing a sequence of about six to about forty amino acid residues that immunologically corresponds substantially to an amino acid residue sequence of the antigenic determinant of interleukin-2, the polypeptide, when linked to a carrier as a conjugate and introduced in an effective amount as a vaccine into a host animal, being capable of inducing production of antibodies in the host that immunoreact with the antigenic determinant of interleukin-2; and (b) a second reagent that contains in biochemically active form an anti-polypeptide antibody that immunoreacts with the synthetic polypeptide, along with a means for indicating the presence of an immunoreaction between the first and second reagents.

The first and second reagents, when admixed in predetermined amounts in the presence of a predetermined amount of body component or culture supernatant to be assayed, provide an amount of immunoreaction that is signalled by the indicating means. The amount of the immunoreaction is different from a known immunoreaction amount when interleukin-2 including the antigenic determinant is not present in the body component.

As indicated, the first reagent contains one of the previously described synthetic polypeptides, a combination of such polypeptides, or polymers or conjugates prepared therefrom. The second reagent includes polyamides containing idiotypic regions of antibodies raised to the synthetic polypeptides or their conjugates (receptors of the first reagent). The idiotype-containing polyamides of the second reagent may be substantially intact antibodies or Fab, Fab' or $F(ab')_2$ antibody fractions whose preparations were described before. An indicating group may also be provided to the system and can be initially bound to or free from either of the two reagents.

Admixture of predetermined amounts of the first and second reagents in the presence of a predetermined amount of a body component to be assayed results in an immunoreaction between the first reagent and the second reagent (its receptor), and the IL-2 and the same receptor. The degree or amount of the immunoreaction so produced between the first and second reagents is different from a known immunoreaction amount when an increased or decreased amount of the IL-2 is present in the body component.

In such a competitive binding assay, the first reagent [IL-2 polypeptide(s) or pure intact IL-2] competes with IL-2 in an unknown sample for binding to a limiting number of binding sites on antibody (receptor) molecules made against IL-2 polypeptide(s). Thus, increasing the amount of unknown IL-2 in the reaction, decreases the binding of antibody to first (solid phase reagent). The amount of immunoreaction between the first and second reagents is typically diminished when an increased amount of the IL-2 is present in the body component, compared to the usual amount present.

In usual practice, a predetermined, known amount of the first reagent is bound to a solid support such as one of the before described ELISA plates. A protein such as BSA that is not bound by the second reagent is then coated on the solid support to block sites of non-specific protein binding on the solid support. The blocking protein that is not bound is thereafter usually removed as by rinsing.

The second reagent and sample to be assayed may be admixed substantially simultaneously with the first, bound reagent. More preferably, predetermined, known amounts of both the second reagent and the sample to be assayed are mixed together to form an immune complex, and then that mixture is admixed with the bound first reagent to bind second reagent that had not formed an immune complex to the first, support-bound reagent. The admixture is maintained for a time sufficient for the first and second reagents to react. The ingredients not bound to the solid support are then removed as by rinsing.

Another diagnostic system comprises the before-discussed anti-idiotype antibodies in biochemically active form and an indicating means. In this system, the anti-idiotype antibodies or their Fab, Fab' or $F(ab')_2$ fractions react with an antigen in a sample to be assayed to form an immuno-reactant whose presence is signalled by the indicating means.

The above system may also include second antibodies raised to antibodies of the same class and from the same species as the anti-idiotype antibodies as part of the indicating means. For example, where the anti-idiotype antibodies are raised in rabbits, commercially available goat anti-rabbit antibodies may be used. Such second antibodies conveniently include a label such as a linked enzyme including horseradish peroxidase (HRP), glucose oxidase or the like; a radioactive element including iodine 125 or 131, hydrogen 3, sulfur 35 or carbon 14; an NMR-active element such as fluorine 19 or nitrogen 15; or a fluorescent dye such as fluorescein.

In another embodiment, antibodies can be provided, for example, to two different antigenic determinants of interleukin-2 according to the procedures previously described. A predetermined amount of the first antibody is bound to a solid support as described above or to wells of a microtiter plate as described hereinafter; and a predetermined amount of the second antibody is labeled with a known amount of an indicating means or group as described, for example, in Section III. In particular, an unknown sample to be assayed for the presence of interleukin-2 activity is admixed with solid-phase bound antibodies made against a synthetic IL-2 polypeptide. The admixture is maintained for a period of time sufficient for the interleukin-2 to bind to the solid-phase bound antibodies and then washed to remove unbound materials. The amount of interleukin-2 bound can then be determined by contacting the bound IL-2 with antibodies raised against a different synthetic IL-2 polypeptide (labeled with an indicating means) and measuring the amount of immunoreaction signalled by the indicating means.

Other immunochemical assay techniques suitable for use in the present invention include at least the following three forms of enzyme immunoassay (EIA): the immunoenzymometric test, the sandwich method for antigen or antibody, and the homogeneous EIA.

The ELISA test was the first to be developed and is patterned after the standard competitive radioimmunoassay (RIA) procedure. As discussed earlier, labeled and unlabeled antigen compete for attachment to a limited quantity of solid-phase antibody. The enzyme label that is displaced is quantitated, and the calculations that follow are essentially the same as in RIA procedures.

In the immunoenzymometric procedure, an unknown quantity of antigen is reacted with an excess of enzyme-labeled antibody, and then a solid-phase antigen for the labeled antibody is added. Centrifugation removes the excess labeled antibody molecules that reacted with the solid-phase antigen, leaving enzymic activity in the soluble phase. The enzyme actively associated with the soluble phase is thereafter measured, and thereby provides a measure of the antigen concentration in the unknown sample.

The sandwich technique relies on the multivalence of antigen and its capacity to bind simultaneously with two different antibody molecules. The first antibody molecule is usually a solid-phase reactant. It is used in excess to ensure binding (complexation) of all the antigen molecules in the unknown sample. After admixture of the sample to be assayed and the antigen-antibody complex-forming reaction is completed, an excess of enzyme-labeled antibody is added and incubated with the complex resulting from the first admixture. The labeled antibody then combines with the available determinants on the antigen. Uncombined labeled antibody is removed by washing and enzyme activity of the bound label is determined. As before, the amount of enzyme bound to the complex is an indirect measure of the amount of antigen in the assayed sample.

Where the principal indicating group or label is an enzyme such as HRP or glucose oxidase, additional reagents are required to visualize the fact that an immune reaction has occurred and the antibody-antigen complex has formed. Such additional reagents for HRP include hydrogen peroxide and an oxidation dye precursor such as diaminobenzidine. Additional reagents useful with glucose oxidase include ABTS dye and glucose.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry.

An indicating group or label is preferably supplied along with the receptor and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Additional diagnostic assays can be employed to determine the presence of an antigenic determinant of IL-2. For example, IL-2 containing cells can be detected by cytoplasmic staining of fixed tissue sections (immunohistology or immunofluorescence - see Section XIII) or by use of a fluorescence-activated cell sorter (flow cytofluorometry).

Flow cytofluorometry using a fluorescence-activated cell sorter (FACS) is one method of separating T and B lymphocytes. In a FACS, droplets are generated by ultrasonic vibration in a small nozzel in such a way that each droplet contains a single cell tagged with a fluorescent label, such as FITC (fluorescein isothiocyanate (or TRITC (tetramethyl rhodamine isothiocyanate). As the droplets pass one by one through a laser beam, each cell is analyzed with regard to the intensity, color and polarization of its fluorescence.

The characteristic signals from individual cells are then analyzed to determine whether the cell meets certain preselected criteria. If it does, the droplet containing the cell is electrically charged and then deflected and separated from the main stream as it passes through an electric field. By attaching appropriate fluorescent antibodies to either T or B cells, one can separate one or the other cell population from a cell suspension.

Thus, affinity-purified IL-2 or synthetic polypeptides that substantially correspond to determinant portions of IL-2 can be used to provide antibodies useful in the detection of IL-2 in biological fluids (culture supernatants, sera and the like) obtained from normal donors or from individuals with various disease states. These antibodies can be used in direct binding or competitive binding assays.

Such binding assays include:

(a) competitive inhibition by unlabeled IL-2 in a sample of the binding of a labeled specific antibody to IL-2 or one of the present synthetic polypeptides bound to a solid support;

(b) competitive inhibition by unlabeled IL-2 in a sample of the binding of a known amount of labeled IL-2 or one of the present synthetic polypeptides to an antibody of this invention bound to a solid support;

(c) the binding of IL-2 in a sample to a first antibody bound to a solid support determined by adding a second labeled antibody. [The first and second antibodies are preferably monoclonal antibodies raised to IL-2 derived polypeptides or to native IL-2, and such antibodies do not cross-react (do not compete for IL-2 binding)];

(d) competitive inhibition by unlabeled IL-2 in a sample of the binding of a labeled anti-idiotypic antibody directed against an IL-2 related monoclonal antibody.

The amount of IL-2 bound to cell surface receptors or binding sites (and thus the amount of cell surface receptors present in a sample) can also be determined as follows.

Cells with IL-2 surface receptors are incubated with unlabeled human IL-2 (or portions thereof). The resulting suspension is maintained for a period of time sufficient for the interleukin-2 to bind to the IL-2 cell surface receptors and the cells are then washed to remove unbound materials. The amount of interleukin-2 bound to the cells can then be determined by contacting the bound IL-2 with antibodies raised against a synthetic IL-2 polypeptide (an anti-polypeptide antibody) labeled with an indicating means and separating any unbound materials. The amount of labeled anti-polypeptide antibody that binds to the IL-2 signalled by the indicating means is a measure of the amount of IL-2 bound to the cell surface receptors. Moreover, the amount of IL-2 bound to the cell surface receptors is proportional to the amount of cell surface receptors in the sample.

In addition, the amount of labeled, affinity-purified human IL-2 (or portions thereof) bound to cell surface receptors or binding sites can be determined. In such a procedure, IL-2 is internally labeled for example, with $^{35}S$-methionine and is affinity-purified on an immunosorbant column as described hereafter in Section V. In the alternative, IL-2 can be affinity purified and then externally labeled with $^{125}I$.

The cells (for example, from a patient with an autoimmune disease) are immobilized on filter discs in 96-well immunofiltration plates, each well being blocked with an appropriate serum- or BSA-containing buffer. The cells are then reacted with increasing concentrations of labeled, affinity-purified IL-2.

Unbound IL-2 is washed from the wells by immunofiltration and the amount of label remaining in each well is determined. Standard curves relating the amount of IL-2 bound to the concentration of IL-2 added to each well can be constructed. Based on the known molecular weight of IL-2 and the specific activity of the labeled IL-2, the data will enable determination of the number of IL-2 molecules (and, thus, the number of cell surface binding sites) bound at saturation.

The non-specific (unsaturable) binding can be determined by performing binding studies in the presence of an excess of unlabeled IL-2. These results are then substrated from the results at saturation to determine specific binding.

V. Affinity Sorbants for IL-2 Purification

Affinity sorbants in which the oligoclonal or monoclonal antibodies of this invention constitute the active, binding portions constitute yet another embodiment of this invention.

In this embodiment, the receptors such as antibodies produced according to this invention are linked to a solid support that is chemically inert to the lymphokine to be purified by those sorbants. The phrase "chemically inert" is used herein to mean that a chemical reaction between the solid support and the lymphokine does not occur. However, physical interactions between the solid support and the lymphokine such as non-specific binding can and do occur between them, although such interactions are preferably minimized.

The solid support can comprise a variety of materials such as cross-linked dextran, e.g. Sephadex G-25, -50, -100, -200 and the like available from Pharmacia Fine Chemicals of Piscataway, NJ, agarose and cross-linked agarose, e.g. Sepharose 6B, CL6B, 4B, CL4B and the like also available from Pharmacia Fine Chemicals; Bio-Gel A-0.5M, A-1.5M, A-50M and the like available from Bio-Rad Laboratories, Richmond, CA; or polyacrylamide beads, e.g. Bio-Gel P-2, P-30, P-100, P-300 and the like also available from Bio-Rad Laboratories. Polyacrylamide beads have the lowest tendency for non-specific binding among the above supports, but also typically have a low porosity that limits their binding capacity. The agarose and cross-linked agarose materials are preferred herein and will be used illustratively as a solid support.

The agarose support is typically activated for linking using cyanogen bromide. The activated support is then washed and linked to the receptor molecules without drying of the activated support. The support-linked receptor is then washed and is ready for use. Unreacted groups on the support can be reacted with an amine such as ethanolamine or Tris, if desired, although the reactivity of those reactive groups decays quickly.

The affinity sorbant can be used in its loose state, as in a beaker or flask, or it can be confined in a column. Prior to use, it is preferable that the affinity sorbant be washed in the buffer or other aqueous medium utilized for lymphokine purification to eliminate non-specifically bound proteins or those receptors that were unstably linked to the support.

An aqueous composition of IL-2 having an amino acid residue sequence corresponding to the amino acid residue sequence of the polypeptide to which the antibodies of the affinity sorbant binds such as serum or a cell extract is provided, and then admixed with the affinity sorbant. That admixture forms a reversible, linked antibody-antigen complex between the antibody and the lymphokine.

The complex is then separated from the remainder of the un-complexed aqueous composition to thereby obtain the lymphokine in purified form reversibly linked to the affinity sorbant. When the admixture takes place in a beaker or flask, this separation can be made by filtration and washing. When the sorbant is in a column, the separation may take place by elution of the un-complexed aqueous medium, again, preferably, followed by a washing step.

When the purified protein is desired free from the affinity sorbant, it can typically be obtained by a variety of procedures. In any of those procedures, the reversibly linked complex is dissociated into its component parts of support-linked antibody and IL-2 followed by separating the IL-2 from the linked-antibody to provide the purified lymphokine free from the affinity sorbant.

The dissociation of the reversible complex may be effected in a number of ways. A 0.2 molar glycine hydrochloride solution at a pH value of about 2.5 is typically used. Alternatively, the bound IL-2 can be competed away from the linked receptor by admixture of the reversible complex with an excess of the immunogenic polypeptide utilized to raise the antibody. Such a competition avoids possible denaturation of the IL-2. Separation of the dissociated IL-2 from the affinity sorbant can be performed as described above.

The preparation of affinity sorbants and their use are well-known. However, such materials and uses that incorporate the oligoclonal antibodies of this invention have not been heretofore available. A detailed description of affinity sorbants, their methods of preparation and uses wherein the antigen is linked to the support can be found in *Antibody as a Tool*, Marchalonis and Warr, eds., John Wiley & Sons, New York, pages 64–67 and 76–96 (1982).

VI. Results

A. ELISA Reactivity of

Rabbit Anti-Polypeptide Sera

Rabbits were immunized with tetanus toxoid or keyhole limpet hemocyanin conjugates of chemically synthesized polypeptides consisting of 13 to 15 amino acid residues whose sequences substantially corresponded to the amino acid residue sequence of a portion of interleukin 2 (IL-2). The resulting sera were examined in an ELISA for reactivity against (recognition of and binding to) the immunizing polypeptide and partially-purified IL-.

Specificity controls included: (a) unrelated polypeptides; (b) mock preparations of human IL-2 (i.e. the supernatant of tonsil-derived cells cultured without mitogen and pooled with supernatant of cultured irradiated lymphoblastoid cells in PHA and PMA); and (c) bovine serum albumin. Additional specificity controls included (d) preimmune sera for the immunized rabbits and (e) hyperimmune rabbit sera specific for synthetic peptides derived from the amino acid residue sequence of the surface antigens of foot and mouth disease virus or hepatitis B virus [in particular, synthetic polypeptides number 65 and 72 of foot and mouth virus and hepatitis as described in Kurz et al., *Nucleic Acid Res*, 9, 1919 (1981) and Valenzuela et al. *Nature*, 280, 815 (1979)].

FIG. 3 shows representative results demonstrating the specificity of rabbit anti-P82 serum (RaP82). Anti-P82 sera had the highest anti-IL-2 titer of the four antisera reactive against IL-2. Anti-P82 sera (RaP82) demonstrated a much stronger reaction against plates coated with the immunizing peptide P82 (panel A) and a tonsil IL-2 preparation (panel B) than did preimmune, norm° 1 rabbit serum (NRS) or rabbit anti-P72 (hepatitis B) serum (RaP72). The anti-P82 serum produced only background level reactivity against an unrelated polypeptide P81 (panel C).

As shown in Table 1, below, all polypeptides, except polypeptide P83, elicited high-titered anti-polypeptide antibodies. Moreover, four of the eight polypeptides elicited antibodies that reacted with a tonsil-derived IL-2 preparation in a solid phase ELISA.

TABLE 1

Representative Antibody Titers of Rabbit Anti-IL-2 Polypeptide Sera

| Polypeptide | Residues[2] | Antibody Titers[1] | |
|---|---|---|---|
| | | Anti-Polypeptide | Anti-IL-2 |
| P10 | 65-78 | $4 \times 10^4$ | 10 |
| P11 | 94-108-C | $2.5 \times 10^4$ | 10 |
| P12 | 111-125 | $1.2 \times 10^5$ | $1 \times 10^2$ |
| P13 | C-126-138 | $3 \times 10^5$ | 30 |
| P81 | 18-32-C | $1 \times 10^6$ | $1 \times 10^2$ |
| P82 | 139-153 | $2 \times 10^5$ | $5 \times 10^3$ |
| P83 | 51-64-C | Negligible | Negligible |
| P84 | 79-92 | $1.2 \times 10^5$ | $5 \times 10^2$ |

[1]Reciprocal dilution producing one-half saturation [50% of maximal optical density (O.D.) at 490 nanometers (nm)].
[2]Based on the published sequence for IL-2 [Taniguchi et al., Nature, 302, 309 (1983)]. C indicates a cysteine residue added to the carboxy- or amino-terminus of the amino acid chain for coupling purposes.

1. Reciprocal dilution producing one-half saturation.
2. Based on the published sequence for IL-2 C indicates a cysteine residue added to the carboxy-or amino-terminus of the amino acid chain for coupling purposes.

Anti-IL-2 antibodies were first detected one week after the third immunization. The concentration of antibody tended to decline thereafter, but the antibodies tended to increase in titer following an additional boost with the polypeptide-carrier conjugate given 6-8 weeks after the third injection. Antibodies remained detectable for longer periods. Anti-IL-2 titers were lower than the respective anti-polypeptide titers (Table 1). No cross reactivity among the different IL-2-derived polypeptides was observed. The same four polypeptides that elicited IL-2-reactive antibodies in rabbits also induced the formation of anti-IL-2 antibodies in mice.

B. Inhibition of Solid Phase ELISA by Soluble Polypeptides

In order to ascertain whether the same antibody population reacts with the immunizing polypeptide and with IL-2, an ELISA was performed in the presence of increasing concentrations of soluble polypeptides.

Figure 4:
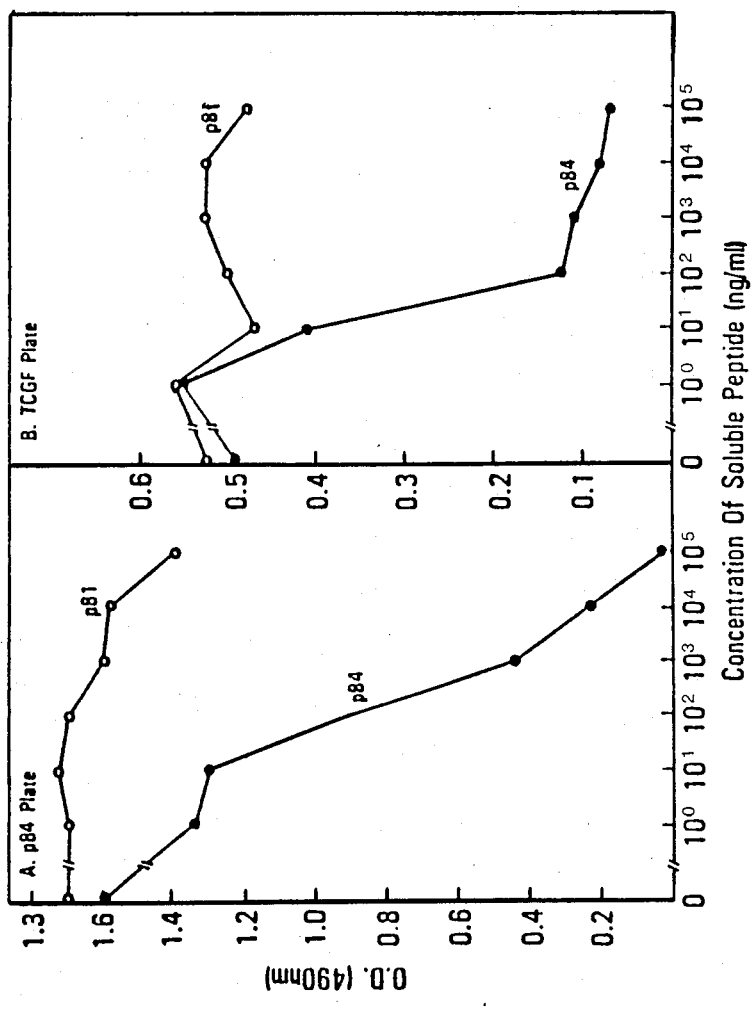
FIG. 4 shows the inhibition of rabbit anti-P84 serum-mediated ELISA by soluble polypeptides. Affinity-purified rabbit anti-P84 serum was incubated in P84-coated or TCGF (IL-2)-coated plates in the absence or presence of increasing concentrations of soluble P81 or P84.

As shown in FIG. 4, the reactivity of anti-P84 serum against solid phase P84 or IL-2 was specifically inhibited by the P84 polypeptide in solution (50 percent inhibition at 10-100 nanograms per milliliter of polypeptide) but not by an unrelated polypeptide, P81. The same restricted population of anti-polypeptide antibodies reacted with IL-2, since a given soluble polypeptide specifically inhibited the binding of the particular anti-polypeptide antibody to IL-2.

C. Reactivity Against Purified Jurkat IL-2

The antisera that demonstrated reactivity against partially-purified tonsil-derived IL-2 were affinity-purified on columns of Affi-gel 10 coupled with the respective polypeptide. Anti-polypeptide antibodies and anti-IL-2 antibodies co-eluted from the column after addition of a pH 2.5 glycine-HCl buffer.

Binding of the affinity-purified antibodies was studied in an ELISA against Jurkat-derived IL-2 purified by AcA-44 chromatography and (isoelectric focusing) IEF. This preparation gave an IL-2 single band on a 10 percent SDS gel and was considered to be 90 percent pure. This represents a human IL-2 preparation that is more pure than the tonsil-derived IL-2 used previously.

Figure 5:
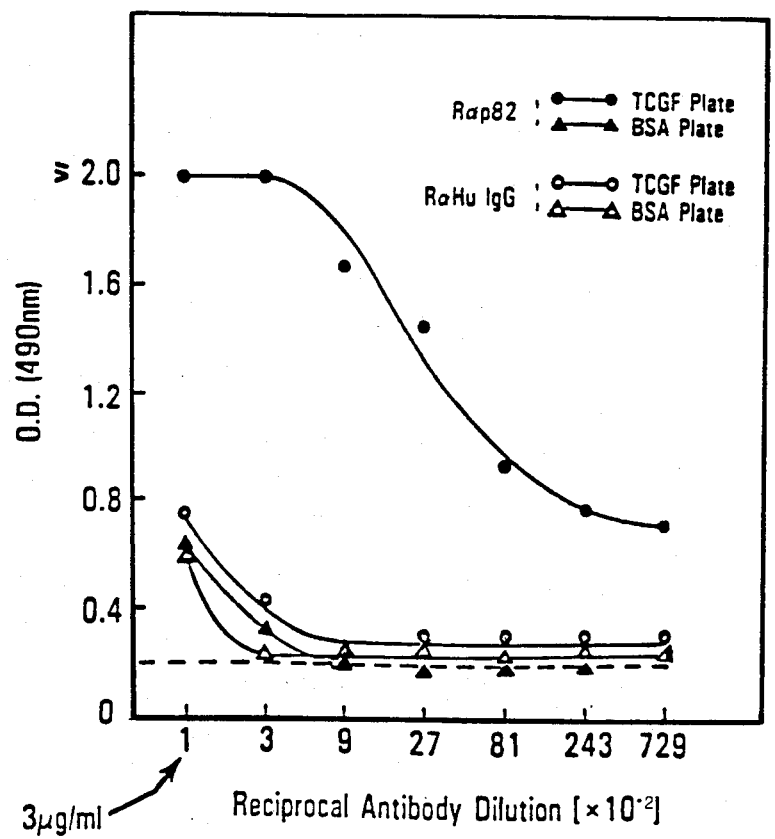
FIG. 5 illustrates the ELISA reactivity of anti-P82 antibodies against purified Jurkat-derived IL-2. Affinity-purified rabbit anti-P82 or anti-human IgG (control) antibodies were titrated on IL-2-coated or BSA-coated plates.

As shown in FIG. 5, affinity-purified anti-P82 antibodies (RαP82) reacted specifically with the purified IL-2 (TCGF). In other, similar, determinations affinity-purified anti-P12 and anti-P84 antibodies also reacted with purified Jurkat IL-2 or recombinant IL-2 while anti-P81 lacked significant activity.

D. Correlation of IL-2 Biological Activity With ELISA Immunoreactivity

Four liters of IL-2-containing crude tonsil supernatants were fractionated on an AcA-44 column and individual fractions were tested for biological activity in an IL-2 bioassay and for immunoreactivity with anti-polypeptide antibodies in a solid-phase ELISA. In the latter case, neat (undiluted) fractions were used to coat the ELISA plates.

Figure 6:
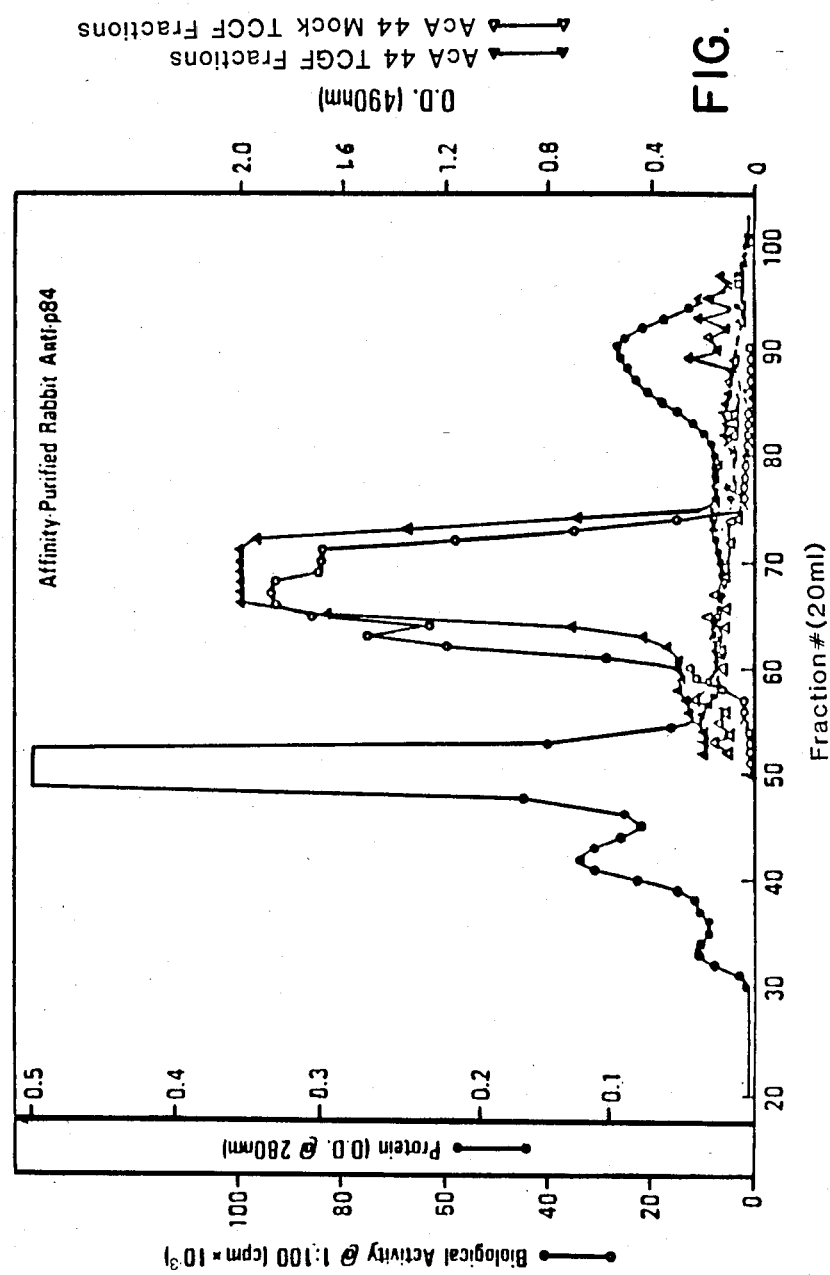
FIG. 6 shows the biological activity and ELISA reactivity profiles of AcA 44-fractionated tonsil-derived IL-2. Samples of 20 milliliter fractions were used undiluted to coat microtiter plates in the ELISA or tested at a dilution of 1:100 for biological activity. Fractions of a mock IL-2 preparation which lacked biological activity were tested in parallel in the ELISA. Affinity-purified rabbit anti-P84 (1:200) was used in the ELISA.

FIG. 6 shows results of a representative determination with an affinity-purified rabbit anti-P84 antibody. An excellent correlation between biological activity and immunoreactivity was found and the peaks of the two activity profiles were similar.

In contrast, AcA-44-derived fractions of a mock IL-2 preparation did not react to any significant extent with the anti-polypeptide antibody. Moreover, an excellent correlation between biological activity and immunoreactivity profiles was found for the after two additional purification steps; specifically, chromatography on Affi-gel blue followed by DEAE-Sephacel chromatography.

A similar correlation was observed with anti-P82 antibodies and, to a lesser degree, with anti-P12 antibodies. These results strongly suggest that the antigen recognized by the anti-polypeptide antibodies in the partially-purified IL-2 preparations is in fact IL-2.

E. Western Blot Analysis

Figure 7:
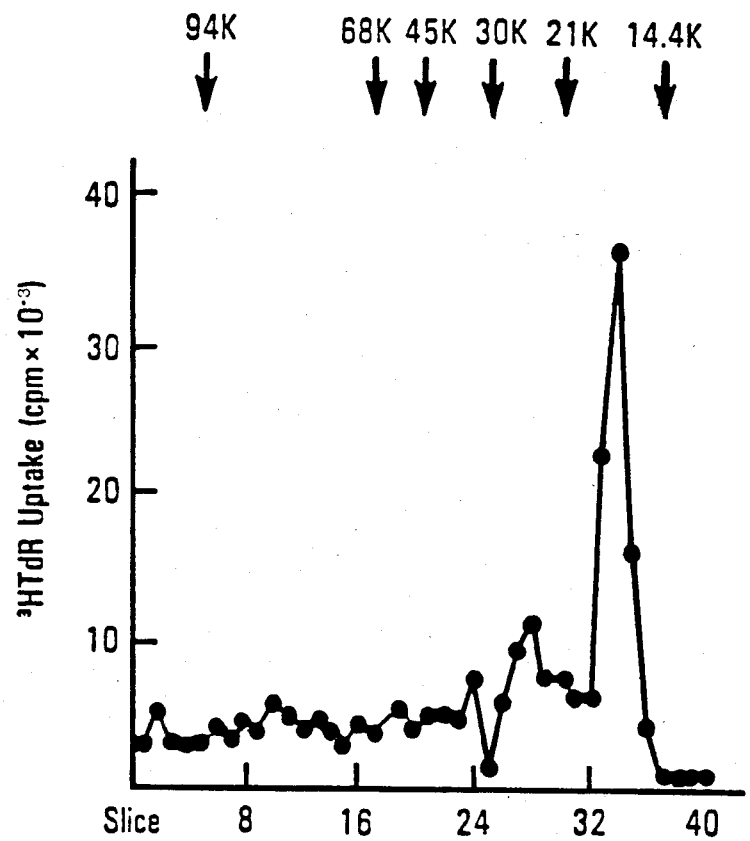
FIG. 7 is Western blot analysis of crude, tonsil-derived, IL-2-containing supernatants using an affinity-purified anti-P84 antibody. Electrophoretically-transferred proteins from a 100×-concentrated supernatant were reacted with 5 micrograms/ml affinity-purified rabbit anti-P84 antibody. Eluates of 2 millimeter thick slices of a parallel gel were tested for IL-2 activity at a dilution of 1:100.

The Western blot technique [Towbin et al., Proc. Natl. Acad. Sci. (USA), 76, 4350 (1979)] was used to further determine the identity of the antigen in the IL-2-containing culture supernatants that reacts with anti-P84 antibodies. Crude, concentrated tonsil-derived supernatants subjected to Western blot analysis revealed two closely-positioned protein bands, in the molecular weight range of 15,000-18,000 daltons, that reacted with the anti-P84 antibody (FIG. 7). Preimmune serum or an unrelated antibody did not react in a similar manner.

Furthermore, biologically-active IL-2 was eluted in a sharp peak from an almost-identical position in the gel (FIG. 7). These results demonstrate that: (a) anti-P84 antibody reacts with a protein or proteins that migrate in a position corresponding to the size of human IL-2 and (b) this protein and the biological activity of IL-2 co-migrate on the gel.

F. Immunofluorescence of PHA-Stimulated Cells

A study was performed to determine whether the anti-polypeptide antibodies react in situ with IL-2-producing cells. PHA-stimulated (or control) human PBL were fixed and were treated with an affinity-purified rabbit anti-P84 antibody and an FITC-conjugated goat anti-rabbit IgG.

Figure 8A:
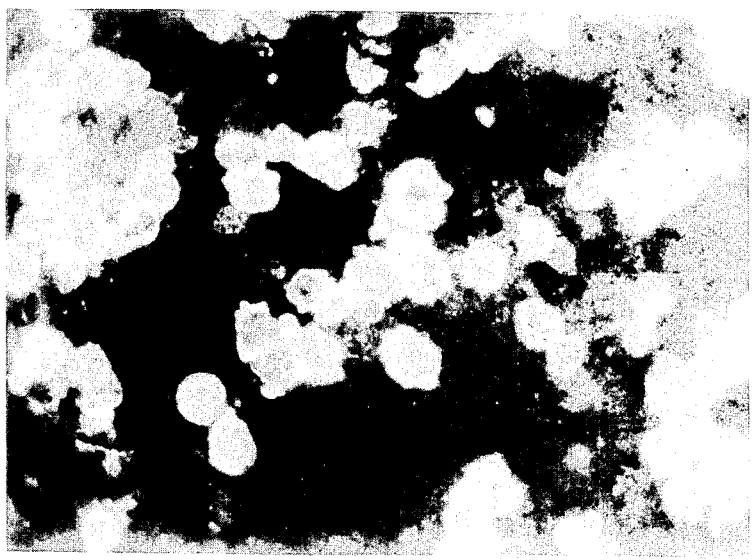
FIG. 8 is a photomicrograph of the immunofluorescent staining of PHA-stimulated PBL by affinity-purified anti-P84 antibody. The anti-P84 antibody was reacted directly with the PBL (panel A) or following preincubation with 20 micrograms/ml P84 (panel B).
Figure 8B:
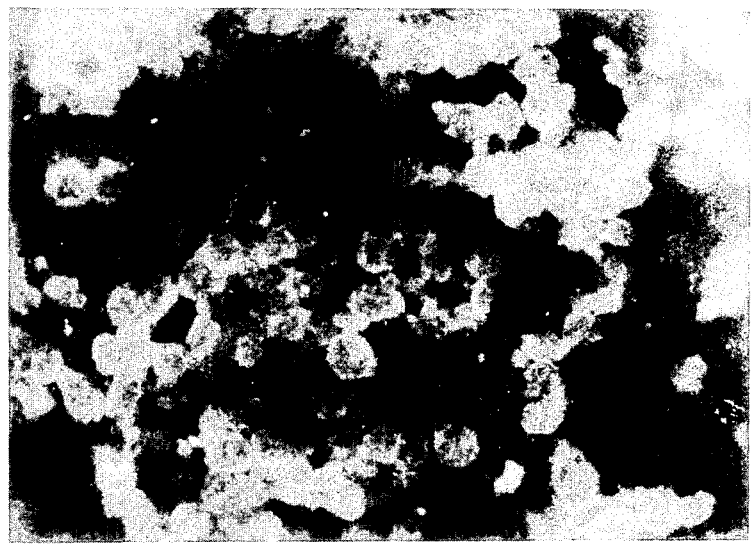

Cytoplasmic staining of PHA-stimulated PBL was observed (See FIG. 8a). Specificity of this reaction was demonstrated because: (a) the staining was eliminated by preincubation of the anti-P84 antibodies with 20 micrograms per milliliter of soluble P84 (FIG. 8b), but not upon preincubation with P81; (b) unstimulated and lipopolysaccharide-stimulated PBL were not stained; and c) PHA-stimulated PBL, treated with an anti-P72 (hepatitis B) antibody, were not stained under the same conditions.

VII. Materials and Methods

A. Production of Human IL-2

IL-2 was derived from human tonsil cells and from the Jurkat human leukemic T cell line. Tonsils removed during routine tonsilectomies were obtained from Children's Hospital of San Diego. Single cell suspensions ($2$–$5 \times 10^9$ cells per donor) were prepared by mincing and tearing the tonsils under aseptic conditions. Jurkat cells (clone 10E4) were obtained from Dr. G. Dennert, Salk Institute for Biological Studies, La Jolla, Calif.

For IL-2 production, cells (both the human tonsil-derived and the Jurkat cells) were cultured at $2 \times 10^6$ cells per milliliter in a culture medium comprising 2 parts RPMI-1640 medium (M.A. Bioproducts, Inc.), 1 part Dulbecco's modified Eagle's medium (DMEM) (M.A. Bioproducts, Inc.) and 1 part Ham's F-12 medium (M.A. Bioproducts, Inc.). The culture medium was supplemented with 4.5 grams per liter glucose, 10 micromolar ethanolamine, 5 micrograms per milliliter each of a mixture of insulin, transferrin and sodium selenite (ITS, Collaborative Research, Inc., Waltham, MA), 50 micrograms per milliliter gentamycin, $5 \times 10^{-5}$ molar 2-mercaptoethanol and 10 micromolar HEPES buffer [4-(2-hydroxyethyl)-1-piperazinethane sulfonic acid].

Production of IL-2 was stimulated in the cells by the addition of a phytomitogen. Phytomitogens are a heterogeneous group of proteins that have few common structural features but are characterized by the following three properties, only the first of which is essential for a protein to be considered phytomitogen: (1) specific binding to sugars, (2) agglutination of cells and (3) stimulation of lymphocytes. Considering these properties, phytomitogens (also referred to as "lectins") resemble antibodies, but differ from antibodies in that lectins are not produced in response to a specific stimulus, lectins are restricted in their specificity to carbohydrates and lectins are not immunoglobulins, but comprise a rather diverse group of proteins.

The three lectins most frequently used in immunology are Concanavalin A (Con A) extracted from jack beans (*Canavalia ensiformis*), phytohemagglutinin (PHA) extracted from kidney beans (*Phaseolus vulgaris*) and pokeweed mitogen (PWM) found in the roots and leaves of pokeweed (*Phytolacca americana*).

Following the addition of a lectin, nondividing lymphocytes grow, differentiate and proliferate; in other words, the lectin acts as a mitosis-stimulating substance (a mitogen). The mitogenic effect can be measured by counting enlarged lymphocytes (blasts) or by determining the increase in the incorporation rate of labeled thymidine, uridine or leucine into DNA, RNA or protein, respectively.

Lectin-stimulated lymphocytes display the same spectrum of functional characteristics as do lymphocytes stimulated by antigens. For example, stimulated B lymphocytes secrete immunoglobulins, whereas stimulated T lymphocytes produce lymphokines that affect the behavior of other cells and can act as cytotoxic cells.

In the present determination, IL-2 production was stimulated in the Jurkat cells with 1 percent phytohemagglutinin-M (PHA-M, Grand Island Biological Co., Grand Island, N.Y.) and 50 nanograms per milliliter phorbol myristate acetate (PMA, P-L Biochemicals, Inc., Milwaukee, Wis.). The tonsil-derived cells were stimulated under similar conditions, but with the addition of irradiated (5,000 rads) Daudi [ATCC CCL 213] or Raji [ATCC CCL 86] lymphoblastoid cell line cells at a concentration of $0.5 \times 10^6$ cells per mililliter.

Mock or analogue IL-2 preparations were made by culturing tonsil cells in the absence of PHA-M and PMA, and by separately culturing irradiated Daudi or Raji lymphoblastoid cells in the presence of PHA-M and PMA. The supernatants of the two separate cultures, that lacked detectable IL-2 activity, were collected and pooled. All supernatants were harvested after 42 hours by centrifugation at 3,000 rotations per minute (rpm) for 15 minutes, filtered and stored frozen. This preparation will be referred to hereafter as a "mock IL-2 preparation".

B. Purification of IL-2

The tonsil-derived supernatants were concentrated 50 to 100 fold by ultrafiltration through a YM-10 membrane (Amicon Corp., Lexington, Mass.). Each concentrated supernatant was purified by sequential chromatography involving passage through a 5 cm$\times$90 cm exclusion column of AcA-44 gel (LKB Produkter AB, Bromma, Sweden) followed by passage through a 2.5 cm x 10 cm affinity column of Affi-gel blue (Bio-Rad, Richmond, CA). Fractions that demonstrated activity in the IL-2 bioassay described in subsection C below were pooled. The active pool was further purified by passage through an AcA-44 chromatography column.

In the alternative, the active pool was subjected to isoelectric focusing (IEF) on a 100 milliliter IEF column (LKB Produkter AB, Sweden) in a pH 3 to 10 ampholine mixture (LKB Produkter AB, Sweden). This procedure resulted in a 1,000 to 3,000-fold purificaton with a 30–50% recovery of the IL-2 biological activity.

IL-2 derived from Jurkat cells was purified by a procedure similar to that described by Robb et al., *J. Exp Med.*, 154, 1455 (1981) but with the following modifications. After concentration on a YM-10 membrane, the cell culture supernatant was fractionated on an AcA-44 column and electrofocused as described above.

C. IL-2 Bioassay

Crude culture supernatants or materials obtained during the different purification steps were tested for IL-2 activity according to the method described by Gillis et al., *J. Immunol.*, 120, 2027 (1978). An IL-2-dependent line, CTLL-2, obtained from Dr. J. Watson of the University of California at Irvine was used as a source of indicator cells.

Briefly, test supernatants were diluted two- or four-fold in 20 microliters of RPMI-1640 medium supplemented with 5 percent fetal calf serum (FCS) and $5 \times 10^{-5}$ molar 2-mercaptoethanol. CTLL-2 cells ($1 \times 10^4$) were added to the diluted test supernatants and incubated at 37 degrees C for 24 hours in a humidified atmosphere of 5 percent carbon dioxide. Cultures were harvested following a 4 hour terminal pulse with 1 microcurie tritiated thymidine ($^3$HTdR, 6.7 Curies per millimole, New England Nuclear, Boston, Mass.) on a Skatron cell harvester (Flow Laboratories, Rockville, MD) and were counted in a liquid scintillation counter.

A tonsil-derived supernatant that routinely gave 50 percent of the maximum $^3$HTdR uptake at a final dilution of approximately 1:40 was arbitrarily assigned an activity of 10 units per milliliter for comparison purposes. The activity in test supernatants was calculated by comparing the dilutions that produced 50 percent of the maximum response using a regression analysis.

VIII. Peptide Syntheses and Selection

A. Synthesis of Polypeptides

Polypeptides including about 15 amino acids to be synthesized were selected from the published sequence of human IL-2 as described in Taniguchi et al., *Nature*, 302, 309 (1983). That selection was based in part on a series of computer analyses to determine the amino acid residue sequences of human IL-2 that are most likely to be exposed on the surface of the native protein. See, for example, Richmond et al., *J. Mol. Biol.*, 119, 537 (1978).

The polypeptides were chemically synthesized by solid-phase methods as described in Merrifield et al., *J. Am. Chem. Soc.*, 85, 2149 (1963) and Houghten et al., *Int. J. Peptide Protein Research*, 16, 311 (1980). The relatively short polypeptides used herein substantially correspond to antigenic determinants of human IL-2.

FIG. 1 shows the 153 amino acid residue sequence of IL-2. The amino acid residue sequences of the eight synthetic polypeptides described herein are shown in FIGS. 1 and 2. In certain instances, a cysteine residue was added to the amino-terminus or the carboxy-terminus of some of the polypeptides to assist in coupling to a protein carrier as described below. The compositions of all polypeptides were confirmed by amino acid analysis.

Generally, an immunogen or synthetic polypeptide is made by the steps of providing a plurality of amino acids which correspond to the amino acid residues of an antigenic determinant domain of interleukin-2 and synthesizing those amino acids into a polypeptide which has a peptide sequence corresponding to the peptide sequence of that antigenic determinant. The produced synthetic polypeptide can be used to produce a vaccine usually by linking it to a carrier to form a conjugate and then dispersing the conjugate in a physiologically tolerable diluent.

The polypeptides are preferably synthesized according to the above-referenced solid phase methods using a cysteine resin. See Merrifield et al., supra. The side chains on individual amino acids are protected as follows: Arg-tosyl, Ser, Thr, Glu and Asp-0-benzyl; Tyr-0-bromobenzyloxy carbamyl; Trp-N-formyl. The N-formyl group on the Trp residues is removed after cleavage of the peptide from the resin support by treatment with 1.0 molar ammonium bicarbonate at a peptide concentration of 1.0 milligram/milliliter for 16 hours at the room temperature. Yamashiro et al., *J. Org. Chem.*, 38, 2594–2597 (1973). The efficiency of coupling at each step can be monitored with ninhydrin or picric acid and is preferably greater than 99 percent in all cases. See Gisin, *Anal. Chem. Aeta*, 58, 248–249 (1972) and Kaiser, *Anal. Biochem.*, 34, 595–598 (1980).

B. Preparation of Polymers

The polypeptides of the present invention can be connected together to form an antigenic polymer comprising a plurality of the polypeptides. Such a polymer has the advantages of increased immunological reaction and where different polypeptides are used to make up the polymer, the additional ability to induce antibodies that immunoreact with several antigenic determinants of interleukin-2.

A polymer can be prepared by synthesizing the polypeptides as discussed above and by adding cysteine residues at both the amino- and carboxy-termini to form a diCys polypeptide. Thereafter, 10 milligrams of the diCYs polypeptide (containing cysteine residues in unoxidized form) are dissolved in 250 milliliters of 0.1 molar ammonium bicarbonate buffer. The dissolved diCys polypeptide is then air oxidized by stirring the resulting solution gently for a period of about 18 hours, or until there is no detectable free mercaptan by the Ellman test. [See Ellman, *Arch. Biochem. Biophys.*, 82:70–77 (1959).] The polymer so prepared contains a plurality of the polypeptides of this invention as repeating units. Those polypeptide repeating units are bonded together by oxidized cysteine residues.

C. Coupling of Polypeptides to Protein Carriers

The synthetic polypeptides were coupled to keyhole limpet hemocyanin (KLH) or tetanus toxoid (TT) by either of the following two methods. In the first method, the carrier was activated with m-maleimido-benzoyl-N-hydroxysuccinimide ester and was subsequently coupled to the polypeptide through a cysteine residue added to the amino- or carboxy-terminus of the polypeptide, as described in Liu et al., *Biochem.*, 80, 690 (1979). In the second method, the -polypeptide was coupled to the carrier through free amino groups, using a 0.04 percent glutaraldehyde solution as is well known. See, for example, Klipstein et al., *J. Infect. Disc.*, 147, 318 (1983).

As discussed before, cysteine residues added at the amino- and/or carboxy-terminii of the synthetic polypeptide have been found to be particularly useful for forming conjugates via disulfide bonds and Michael addition reaction products, but other methods well known in the art for preparing conjugates can also be used. Exemplary additional binding procedures include the use of dialdehydes such as glutaraldehyde (discussed above) and the like, or the use of carbodiimide technology as in the use of a water-soluble carbodiimide, e.g. 1-ethyl-3-(3-dimethylaminopropyl) carbodiimide.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such asسheep erythrocytes (SRBC), tetanus toxoid, as well as polyamino acids such as poly(D-lysine:D-glutamic acid), and the like.

As is also well known in the art, it is often beneficial to bind the synthetic polypeptide to its carrier by means of an intermediate, linking group. As noted above, glutaraldehyde is one such linking group. However, when cysteine is used, the intermediate linking group is preferably an m-maleimidobenzoyl N-hydroxysuccinimide ester (MBS). MBS is typically first added to the carrier by an ester-amide interchange reaction. Thereafter, the above Michael reaction can be followed, or the addition can be followed by addition of a blocked mercapto group such as thiolacetic acid ($CH_3COSH$) across the maleimido-double bond. After cleavage of the acyl blocking group, a disulfide bond is formed between the deblocked linking group mercaptan and the mercaptan of the added cysteine residue of the synthetic polypeptide.

The choice of carrier is more dependent upon the ultimate intended use of the antigen than upon the determinant portion of the antigen, and is based upon criteria not particularly involved in the present invention. For example, if a vaccine is to be used in animals, a carrier that does not generate an untoward reaction in the particular animal should be selected. If a vaccine is to be used in man, then the overriding concerns involve the lack of immunochemical or other side reaction of the carrier and/or the resulting antigen, safety and efficacy--the same considerations that apply to any vaccine intended for human use.

IX. Immunization Procedures

The inocula or vaccines used herein contain the stated amount of polypeptide alone, as a polymer of individual polypeptides linked together through reaction with glutaraldehyde or as a conjugate linked to a carrier. These inocula may contain polypeptide termini followed by oxidation with, for example, atmospheric oxygen at moderate pH values between about pH 7 and pH 10 and at polypeptide concentrations of about 20 micrograms to about 500 milligrams per inoculation. The stated amounts of polypeptide refer to the weight of polypeptide without the weight of a carrier, when a carrier was used.

The inocula also contained a physiologically tolerable (acceptable) diluent such as water or saline, and further typically included an adjuvant. Adjuvants such as complete Freund's adjuvant (CFA), incomplete Freund's adjuvant (IFA) and alum are materials well known in the art, and are available commercially from several sources.

Inocula stock solutions were prepared with CFA, IFA or alum as follows: An amount of the synthetic polypeptide, polymeric polypeptide or conjugate sufficient to provide the desired amount of polypeptide per inoculation was dissolved in phosphate-buffered saline (PBS) at a pH value of 7.2 or any other appropriate pH value. Equal volumes of CFA, IFA or alum were then mixed with the polypeptide solution to provide an inoculum containing polypeptide, water and adjuvant in which the water-to-oil ratio was about 1:1. The mixture was thereafter homogenized to provide the inocula stock solution.

Rabbits were injected intramuscularly with an inoculum comprising 300 to 400 micrograms of a polypeptide conjugate emulsified in complete Freund's adjuvant (CFA), incomplete Freund's adjuvant (IFA), or mixed with alum (5 milligrams per milliliter in each instance) on days 0, 14 and 21, respectively. Each immunization consisted of four intramuscular injections of the inoculum in the flanks of the animal. Mice were immunized in a similar way using one tenth of the above dose per injection.

Animals were bled 7 and 14 days after the last injection. In some cases, the animals received booster injections in alum, and were bled thereafter as necessary. Control pre-immune serum was obtained from each animal by bleeding just before the initial immunization.

Inocula stock solutions can also be prepared with keyhole limpet hemocyanin (KLH), KLH in IFA (incomplete Freund's adjuvant), KLH-alum absorbed, KLH-alum absorbed-pertussis, edestin, thyroglobulin, tetanus toxoid and tetanus toxoid in IFA.

Upon injection or other introduction of the antigen or inoculum into the host, the immune system of the host responds by producing large amounts of antibody to the antigen. Since the specific antigenic determinant of the manufactured antigen, i.e., the antigen formed from the synthetic polypeptide and the carrier immunologically corresponds substantially to the determinant of the natural antigen of interest, the host becomes immune to the natural antigen. In the case where the invention is used as a vaccine, this is the desired result.

The effective amount of polypeptide per inoculation depends, among other things, on the species of animal inoculated, the body weight of the animal and the chosen inoculation regimen as is well known. Inocula are typically prepared from the dried solid polypeptide or polypeptide polymer by suspending the polypeptide or polypeptide polymer in water, saline or adjuvant, or by binding the polypeptide to a carrier and suspending the carrier-bound polypeptide (conjugate) in a similar physiologically tolerable diluent such as an adjuvant (as previously described). An effective amount of polypeptide present in a vaccine can be from about 20 micrograms to about 500 milligrams per inoculation, not including the weight of the carrier.

X. Diagnostics

Sera or affinity-purified antibodies (as body samples) were studied in an enzyme-linked immunosorbent assay (ELISA). Round-bottom Immulon 2 microtiter plates (Dynatech Laboratories, Inc., Alexandr-ia, VA) having 96 wells per plate were coated with solutions of the polypeptides (500 nanograms per milliliter), partially-purified IL-2 (50 to 100 units per milliliter) or 1 percent bovine serum albumin (BSA). Serial dilutions of sera in 1 percent BSA buffer were added to the plates to block non-specific protein binding sites in the wells of the plates. The plates were then maintained (incubated) for 1 hour at 37 degrees C. and washed 8 times with a phosphate-buffered saline (PBS) solution (pH 7.2) containing 0.05 percent polyoxyethylene (20) sorbitan monolaurate (TWEEN 20).

The plates were then maintained for one hour at 37 degrees C with a 1:2000 dilution of affinity-purified, horseradish peroxidase(HRP)-conjugated goat anti-mouse IgG +IgM to measure mouse antibodies or goat anti-rabbit IgG to measure rabbit antibodies (Tago Inc., Burlingame, Calif.).

Thereafter, the plates were washed with water and the peroxidase labeled antibodies bound to the solid support were reacted with a solution of 0.4 milligrams per milliliter ortho-phenylenediamine and 0.006 percent hydrogen peroxide (both obtained from Sigma Chemical Co., St. Louis, Mo.) in a pH 5.0 citrate-phosphate buffer to develop the color label. The reaction was stopped after 15–30 minutes in the dark by adding 50 microliters of 2 molar sulfuric acid. Absorbance was determined at 490 nanometers in a model MR600 Microplate Reader (Dynatech Laboratories, Inc., Alexandria, Va.).

The amount of antibody in the serum required to saturate one-half of the polypeptide and one-half of the IL-2 that were coated on each plate was thereafter calculated using standard techniques. Those results are shown hereafter in Table 1 of Section VI(A).

XI. Affinity Purification of Rabbit Anti-Polypeptide Antibodies

Two milligrams of polypeptide were dissolved in 1 milliliter of 100 millimolar 3-N-morpholinopropane-sulfonic acid (MOPS) buffer (pH 7.5) added to 2 milliliters of washed Affi-gel 10 (Bio-Rad, Richmond, Va.) and maintained at 4 degrees C. overnight. Unreacted groups on the gel were blocked with 1/10 volume of 1 molar ammonium chloride for 1 hour at room temperature (23° C.). The gel-coupled polypeptide was then washed with PBS, followed by washing with 100 millimolar glycine-HCl buffer (pH 2.5) and packed in a 1×2 centimeter column of a plastic syringe.

Immune rabbit serum (5-20 milliliters) was added to the column at a flow rate of 20-40 milliliters per hour. The column was washed with PBS and bound antibody was eluted with 100 millimolar glycine-HCl buffer at pH 2.5. The acid eluates (2 milliliters per fraction) were neutralized with 1/20 volume of 1 molar Tris-HCl buffer (2-amino-2-hydroxymethyl-1,3-propanediol).

Fractions were studied in an ELISA, as described above, on polypeptide-coated or IL-2-coated plates, and their protein content was determined by the Lowry method as described in Lowry et al., *J. Biol. Chem.*, 193, 265 (1951). Active eluate fractions were pooled, concentrated to 1-5 milligrams protein per milliliter, dialyzed against PBS, followed by dialysis against 100 MOPS buffer, pH 7.5, and stored at minus 20 degrees C.

XII. Western Blot Analyses

Protein constituents in crude 100-fold concentrated IL-2-containing supernatants were separated by sodium dodecyl sulfate (SDS)-polyacrylamide gel electrophoresis as described in Laemmli, *Nature*, 227, 580 (1970), and were then electrophoretically blotted onto nitrocellulose paper as described in Towbin et al., *Proc. Natl. Acad. Science USA*, 76, 4350 (1979).

The blots were blocked to minimize non-specific binding by the antibodies and labeled with affinity purified anti-P84 antibody (5 micrograms per milliliter) using a modification of standard procedures as described in [Johnson et al., *Gene Anal Tech.* 1, 3 (1984)].

The blocked and labeled blots were then washed three times with blocking buffer [Johnson et al., *Gene Anal. Tech.* 1, 3 (1984)] and maintained for 1 hour at room temperature with $^{125}$I-*Staphylococcus aureus* protein A at a concentration of $1 \times 10^6$ counts per minute per gel lane. The radiolabeled protein A provides a label for the presence of IgG antibodies via a complexation reaction.

The protein A labeled blots were washed extensively as above, rinsed with water, dried and subjected to autoradiography. A parallel gel was cut into a plurality of 2 millimeter thick slices and the slices were eluted by mincing and incubating them in 300 microliters of 5 percent FCS-supplemented culture medium for 16 hours at 37 degrees C. The medium was then incubated at 4 degrees C. for 4 hours to precipitate the SDS from the gels. The precipitate was removed by centrifugation and the supernatants were tested for IL-2 activity as described above.

XIII. Immunofluorescence

Human peripheral blood lymphocytes (PBL) were separated from heparinized blood by Ficoll-Hypaque centrifugation (Histopaque-1077, Sigma Chemical Co., St. Louis, Mo.). The cells were cultured at $2 \times 10^6$ cells per milliliter in RPMI-1640 medium plus 5 percent fetal calf serum (FCS) in the absence or presence of 0.5 percent phytohemagglutinin-M. The cells were harvested two days later, washed twice, and pelleted on glass slides using a cytocentrifuge.

The slides were fixed for 5 minutes with methanol, washed with water and incubated for 30 minutes at room temperature with 10 to 50 micrograms per milliliter anti-IL-2 polypeptide antibody or control antibody in PBS and 10 percent FCS. After washing the slides with water, each slide was treated with a 1:50 dilution of fluorescein isothiocyanate (FITC)-conjugated goat anti-rabbit IgG (Cappel Laboratories, Cochranville, PA) for 30 minutes at 4 degrees C, washed with water and observed in a Zeiss microscope under phase and fluorescence microscopy.

The foregoing is intended as illustrative of the present invention but is not limiting. Numerous variations and modifications can be made without departing from the spirit and scope of the novel concepts of the invention. It should be understood that no limitation with respect to the specific antibodies, compositions and use described herein is intended or should be inferred.

What is claimed is:

1. A synthetic polypeptide containing about 6 to about 40 amino acid residues having an amino acid residue sequence that substantially corresponds to an amino acid residue sequence of interleukin-2 that is selected from the group consisting of:
    (a) the interleukin-2 protein from about position 18 to about position 32 from the amino-terminus thereof,
    (b) the interleukin-2 protein from about position 79 to about position 92 from the amino-terminus thereof,
    (c) the interleukin-2 protein from about position 111 to about position 125 from the amino-terminus thereof, and
    (d) the interleukin-2 protein from about position 139 to about position 153 from the amino-terminus thereof;
    said synthetic polypeptide having the capacity alone, as a polymer or as a conjugate of said polypeptide bound to a carrier, when injected into a host in an effective amount and in a physiologically tolerable diluent of inducing the production of antibodies to interleukin-2.

2. The synthetic polypeptide according to claim 1 wherein said synthetic polypeptide contains from about 10 to about 20 amino acid residues.

3. The synthetic polypeptide according to claim 1 including the sequence of amino acid residues, taken from left to right and in the direction from amino-terminus to carboxy-terminus, represented by the formula and selected from the group consisting of:
    ThrAsnSerAlaProThrSerSerSerThrLysLysThrGlnLeu,
    LeuGluGluGluLeuLysProLeuGluGluValLeuAsnLeu,
    ValIleValLeuGluLeuLysGlySerGluThrThrPheMetCys;and
    AsnArgTrpIleThrPheCysGlnSerIleIleSerThrLeuThr.

4. The synthetic polypeptide according to claim 1 including the sequence of amino acid residues, taken from left to right and in the direction from amino-terminus to carboxy-terminus, represented by the formula:
    ThrAsnSerAlaProThrSerSerSerThrLysLysThrGlnLeu.

5. The synthetic polypeptide according to claim 1 including the sequence of amino acid residues, taken from left to right and in the direction from amino-terminus to carboxy-terminus, represented by the formula:
LeuGluGluGluLeuLysProLeuGluGluValLeuAsnLeu.

6. The synthetic polypeptide according to claim 1 including the sequence of amino acid residues, taken from left to right and in the direction from amino-terminus to carboxy-terminus, represented by the formula:
ValIleValLeuGluLeuLysGlySerGluThrThrPheMetCys.

7. The synthetic polypeptide according to claim 1 including the sequence of amino acid residues, taken from left to right and in the direction from amino-terminus to carboxy-terminus, represented by the formula:
AsnArgTrpIleThrPheCysGlnSerIleIleSerThrLeuThr.

8. The synthetic polypeptide according to claim 1 wherein said physiologically tolerable diluent is a member of the group consisting of water, saline and an adjuvant.

9. The synthetic polypeptide according to claim 1 wherein said carrier is selected from the group consisting of keyhole limpet hemocyanin, keyhole limpet hemocyanin in incomplete Freund's adjuvant, alum, keyhole limpet hemocyanin-alum absorbed, keyhole limpet hemocyanin-alum absorbed-pertussis, edestin, thyroglobulin, tetanus toxoid and tetanus toxoid in incomplete Freund's adjuvant.

10. An inoculum comprising an effective amount of synthetic polypeptide containing about 6 to about 40 amino acid residues having an amino acid residue sequence that immunologically corresponds substantially to an amino acid residue sequence of interleukin-2 that is selected from the group consisting of:
(a) the interleukin-2 protein from about position 18 to about position 32 from the amino-terminus thereof,
(b) the interleukin-2 protein from about position 79 to about position 92 from the amino-terminus thereof,
(c) the interleukin-2 protein from about position 111 to about position 125 from the amino-terminus thereof, and
(d) the interleukin-2 protein from about position 139 to about position 153 from the amino-terminus thereof;
and a physiologically tolerable diluent, said inoculum, when introduced into a host, being capable of inducing the production of antibodies in the host that immunoreact with interleukin-2.

11. The inoculum according to claim 10 wherein said synthetic polypeptide contains from about 10 to about 20 amino acid residues.

12. The inoculum according to claim 10 wherein said synthetic polypeptide includes the sequence of amino acid residues, taken from left to right and in the direction from amino-terminus to carboxy-terminus, represented by the formula and selected from the group consisting of:
ThrAsnSerAlaProThrSerSerSerThrLysLysThrGlnLeu,
LeuGluGluGluLeuLysProLeuGluGluValLeuAsnLeu,
ValIleValLeuGluLeuLysGlySerGluThrThrPheMetCys;and
AsnArgTrpIleThrPheCysGlnSerIleIleSerThrLeuThr.

13. The inoculum according to claim 10 wherein said synthetic polypeptide includes the sequence of amino acid residues, taken from left to right and in the direction from amino-terminus to carboxy-terminus, represented by the formula:
ThrAsnSerAlaProThrSerSerSerThrLysLysThrGlnLeu.

14. The inoculum according to claim 10 wherein said synthetic polypeptide includes the sequence of amino acid residues, taken from left to right and in the direction from amino-terminus to carboxy-terminus, represented by the formula:
LeuGluGluGluLeuLysProLeuGluGluValLeuAsnLeu.

15. The inoculum according to claim 10 wherein said synthetic polypeptide includes the sequence of amino acid residues, taken from left to right and in the direction from amino-terminus to carboxy-terminus, represented by the formula:
ValIleValLeuGluLeuLysGlySerGluThrThrPheMetCys.

16. The inoculum according to claim 10 wherein said synthetic polypeptide includes the sequence of amino acid residues, taken from left to right and in the direction from amino-terminus to carboxy-terminus, represented by the formula:
AsnArgTrpIleThrPheCysGlnSerIleIleSerThrLeuThr.

17. The inoculum according to claim 10 wherein said physiologically tolerable diluent is a member of the group consisting of water, saline and an adjuvant claim 10.

18. The inoculum according to wherein said synthetic polypeptide is bound to a carrier.

19. The inoculum according to claim 18 wherein said carrier is selected from the group consisting of keyhole limpet hemocyanin, keyhole limpet hemocyanin in incomplete Freund's adjuvant, alum, keyhole limpet hemocyanin-alum absorbed, keyhole limpet hemocyanin-alum absorbed-pertussis, edestin, thyroglobulin, tetanus toxoid and tetanus toxoid in incomplete Freund's adjuvant.

20. Antibodies raised in an animal host to a synthetic polypeptide containing about 6 to about 40 amino acid sequence that immunologically corresponds substantially to an amino acid residue sequence of interleukin-2 that is selected from the group selected from:
(a) the interleukin-2 protein from about position 18 to about position 32 from the amino-terminus thereof,
(b) the interleukin-2 protein from about position 79 to about position 92 from the amino-terminus thereof,
(c) the interleukin-2 protein from about position 111 to about 125 from the amino-terminus thereof, and
(d) the interleukin-2 protein from about position 139 to about position 153 from the amino terminus thereof;
said antibodies having the capacity to immunoreact with interleukin-2.

21. Antibodies according to claim 20 wherein said synthetic polypeptide includes a sequence of amino acid residues, taken from left to right and in the direction from amino-terminus to carboxy-terminus, represented by the formula and selected from the group consisting of:
ThrAsnSerAlaProThrSerSerSerThrLysLysThrGlnLeu;
LeuGluGluGluLeuLysProLeuGluGluValLeuAsnLeu, ValIleValLeuGluLeuLysGlySerGluThrThrPhe-MetCys;and AsnArgTrpIleThrPheCysGlnSerIleIleSerThrLeuThr.

22. A diagnostic system for assaying for the presence of interleukin-2 comprising in biochemically active form antibodies raised in an animal host to a synthetic polypeptide containing about 6 to about 40 amino acid residues having an amino acid residue sequence that immunologically coresponds to at least a portion of interleukin-2 that is selected from the group consisting of:
  (a) the interleukin-2 protein from about positions 18 to about 32 from the amino-terminus thereof,
  (b) the interleukin-2 protein from about position 79 to about position 92 from the amino-terminus thereof,
  (c) the interleukin-2 protein from about position 111 to about position 125 from the amino-terminus thereof, and
  (d) the interleukin-2 protein from about position 139 to about position 153 from the amino terminus thereof;
said antibodies immunoreacting with an admixed sample to be assayed that contains interleukin-2 to form an immunoreactant with interleukin-2, the presence of said immunoreactant being signalled by an indicating means.

23. The diagnostic system according to claim 22 wherein said synthetic polypeptides includes the sequence of amino acid residues, taken from left to right and in the direction from amino-terminus to carboxy-terminus, represented by the formula and selected from the group consisting of:
  ThrAsnSerAlaProThrSerSerSerThrLysLysThrGlnLeu,
  LeuGluGluGluLeuLysProLeuGluGluValLeuAsnLeu,
  ValIleValLeuGluLeuLysGlySerGluThrThrPhe-MetCys;and
  AsnArgTrpIleThrPheCysGlnSerIleIleSerThrLeuThr.

24. The diagnostic system according to claim 22 further including an indicating means comprising enzyme-linked second antibodies, said second antibodies being raised to antibodies of the same class and from the same species as the first named antibodies, and signalling said immunoreaction by binding to said first named antibodies present in said immunoreactant, said signal being indicated by the reaction of said linked enzyme with an added substrate.

25. The diagnostic system according to claim 22 wherein said indicating means comprises a radioactive element bonded to said antibodies and said immunoreaction causes precipitation of said immunoreactant containing said radioactive element.

26. A diagnostic system for assaying for the presence of interleukin-2 in a body component comprising in separate containers
  (i) a first reagent that contains in biologically active form a synthetic polypeptide containing a sequence of about six to about forty amino acid residues that immunologically corresponds substantially to an amino acid residue sequence of interleukin-2 that is selected from the group consisting of:
    (a) the interleukin-2 protein from about position 18 to about position 32 from the amino terminus thereof,
    (b) the interleukin-2 protein from about position 79 to about position 92 from the amino terminus thereof,
    (c) the interleukin-2 protein form about position 111 to about position 125 from the amino terminus thereof, and
    (d) the interleukin-2 protein from about position 139 to about position 153 from the amino terminus thereof;
  said polypeptide, when linked to a carrier as a conjugate and introduces in an effective amount as an inoculum into a host animal, being capable of inducing production of antibodies in the host that immunoreact with interleukin-2; and
  (ii) a second reagent that contains in biochemically active form an anti-polypeptide antibody that immunoreacts with said synthetic polypeptide; along with a means for indicating the presence of an immunoreaction between said first and second reagents; said first and second reagents, when admixed in predetermined amounts in the presence of a predetermined amount of body component to be assayed, providing an amount of immunoreaction signalled by said indicating means, the amount of said immunoreaction being different from a known immunoreaction amount when interleukin-2 is not present in said body component.

27. A method for assaying for the presence of an antigenic determinant of interleukin-2 in a sample comprising:
  (a) providing an anti-polypeptide antibody to a synthetic polypeptide of claim 1;
  (b) admixing a predetermined amount of said anti-polypeptide antibody with a predetermined amount of sample to be assayed for the presence of the antigenic determinant to which the anti-polypeptide antibody binds;
  (c) maintaining that admixture for a period of time sufficient for said anti-polypeptide antibody to bind to the antigenic determinant present in the admixed sample; and
  (d) determining the amount of binding between said anti-polypeptide antibody and said antigenic determinant of interleukin-2.

28. An affinity sorbant comprising an inert, solid support having linked thereto in biochemically active form antibodies raised in an animal host to a synthetic polypeptide containing about 6 to about 40 amino acid residues having an amino acid sequence that imaunologically corresponds substantially to an amino acid residue sequence of interleukin-2 that is selected from the group consisting of:
  (a) the interleukin-2 protein from about position 18 to about position 32 from the amino-terminus thereof,
  (b) the interleukin-2 protein from about position 79 to about position 92 from the amino-terminus thereof,
  (c) the interleukin-2 protein from about position 111 to about position 125 from the amino-terminus thereof, and
  (d) the interleukin-2 protein from about position 139 to about position 153 from the amino-terminus there;
said affinity sorbant forming a reversible complex when admixed with an aqueous composition containing interleukin-2.

29. A synthetic polypeptide having an amino acid residue sequence, taken from left to right and in the direction of amino-terminus to carboxy-terminus, represented by the formula:
  ThrAsnSerAlaIroThrSerSerSerThrLysLy
and the pharmaceutically acceptable salts thereof.

30. A synthetic polypeptide having an amino acid residue sequence, taken from left to right and in the direction of amino-terminus to carboxy-terminus, represented by the formula:

LeuGluGluGluLeuLysProLeuGluGluValLeuAsnLe and the pharmaceutically acceptable salts thereof.

31. A sythetic polypeptide having an amino acid residue sequence, taken from left to right and in the direction of amino-terminus to carboxy-terminus, represented by the formula:

ValIleValLeuGluLeuLysGlySerGluThrThrPh and the pharmaceutically acceptable salts thereof.

32. A synthetic polypeptide having an amino acid residue sequence, taken from left to right and in the direction of amino-terminus to carboxy-terminus, represented by the formula:

AsnArgTrpIleThrPheCysGluSerIleIleSerTh and the pharmaceutically acceptable salts thereof.

* * * * *

UNITED STATES PATENT AND TRADEMARK OFFICE
CERTIFICATE OF CORRECTION

PATENT NO. : 4,636,463

DATED : January 13, 1987

INVENTOR(S) : Amnon Altman, et al.

It is certified that error appears in the above-identified patent and that said Letters Patent is hereby corrected as shown below:

Column 3, lines 56-57, delete "Gl-n" and insert --Gln--

Column 3, lines 62-63, delete "Th-r" and insert --Thr--

Column 4, line 31, delete "recombin-ant", and insert --recombinant--

Column 4, line 40, delete "monclonal", and insert --monoclonal--

Column 8, line 44, delete "monclonal" and insert --monoclonal--

Column 9, line 38, delete "of", first occurrence, and insert --or--

Column 20, line 44, delete "IL-" and insert --IL-2--

Column 20, lines 66-67, delete "norm°l" and insert --normal--

Column 21, lines 25-28, delete in their entirety

Column 24, line 12, delete "mililliter" and insert --milliliter--

Column 24, line 42, delete "purificaton" and insert --purification--

Column 26, line 9, delete "diCYs" and insert --diCys--

Column 26, line 31, delete "-polypeptide" and insert --polypeptide--

Column 26, line 34, delete "Disc." and insert --Dis.--

UNITED STATES PATENT AND TRADEMARK OFFICE
CERTIFICATE OF CORRECTION

PATENT NO. : 4,636,463

DATED : January 13, 1987

INVENTOR(S) : Amnon Altman, et al.

It is certified that error appears in the above-identified patent and that said Letters Patent is hereby corrected as shown below:

Column 28, line 32, delete "Alexandr-ia" and insert --Alexandria--

Column 29, line 43, delete "Anal" and insert --Anal.--

Claim 3, lines 6-7, delete "Gl-n" and insert --Gln--

Claim 3, lines 12-13, delete "Th-r", second occurrence, and insert --Thr--

Claim 4, lines 5-6, delete "Gl-n" and insert --Gln--

Claim 7, lines 5-6, delete "Th-r", second occurrence, and insert --Thr--

Claim 12, lines 7-8, delete "Gl-n" and insert --Gln--

Claim 12, lines 13-14, delete "Th-r", second occurrence, and insert --Thr--

Claim 13, lines 6-7, delete "Gl-n" and insert --Gln--

Claim 16, lines 6-7, delete "Th-r", second occurrence, and insert --Thr--

Claim 17, lines 3-4, delete "claim 10"

Claim 18, line 1, after "to", insert --claim 10--

Claim 20, line 11, before "125", insert --position--

Claim 21, lines 7-8, delete "Gl-n" and insert --Gln--

UNITED STATES PATENT AND TRADEMARK OFFICE
CERTIFICATE OF CORRECTION

PATENT NO. : 4,636,463                    Page 3 of 4

DATED : January 13, 1987

INVENTOR(S) : Amnon Altman, et al.

It is certified that error appears in the above-identified patent and that said Letters Patent is hereby corrected as shown below:

Claim 21, lines 13-14, delete "Th-r", second occurrence, and insert --Thr--

Claim 22, line 6, delete "coresponds" and insert --corresponds--

Claim 23, lines 7-8, delete "Gl-n" and insert --Gln--

Claim 23, lines 13-14, delete "Th-r", second occurrence, and insert --Thr--

Claim 26, line 14, delete "form" and insert --from--

Claim 26, line 21, delete "introduces" and insert --introduced--

Claim 28, lines 5-6, delete "imaunologically" and insert --immunologically--

Claim 29, line 5, delete "Thr Asn Ser Ala Iro Thr Ser Ser Ser Thr Lys Ly" and insert --Thr Asn Ser Ala Pro Thr Ser Ser Ser Thr Lys Lys Thr Glu Leu--

Claim 30, line 6, delete "As-n" and insert --Asn--

UNITED STATES PATENT AND TRADEMARK OFFICE
CERTIFICATE OF CORRECTION

PATENT NO. : 4,636,463

DATED : January 13, 1987

INVENTOR(S) : Amnon Altman, et al.

It is certified that error appears in the above-identified patent and that said Letters Patent is hereby corrected as shown below:

Claim 31, line 1, delete "sythetic" and insert --synthetic--

Claim 31, line 5, delete "Ph" and insert --Phe Met Cys--

Claim 32, line 5, delete "Th" and insert --Thr Leu Thr--

Signed and Sealed this

Twenty-third Day of August, 1988

Attest:

DONALD J. QUIGG

Attesting Officer

Commissioner of Patents and Trademarks